(12) United States Patent
Gilman

(10) Patent No.: US 9,303,263 B2
(45) Date of Patent: Apr. 5, 2016

(54) APTAMERS THAT BIND CD271

(71) Applicant: Vivonics, Inc., Waltham, MA (US)

(72) Inventor: Vladimir Leo Gilman, Westford, MA (US)

(73) Assignee: VIVONICS, INC., Waltham, MA (US)

( * ) Notice: Subject to any disclaimer, the term of this patent is extended or adjusted under 35 U.S.C. 154(b) by 0 days.

(21) Appl. No.: 14/382,681

(22) PCT Filed: Feb. 28, 2014

(86) PCT No.: PCT/US2014/019284
§ 371 (c)(1),
(2) Date: Sep. 3, 2014

(87) PCT Pub. No.: WO2014/134403
PCT Pub. Date: Sep. 4, 2014

(65) Prior Publication Data
US 2015/0376619 A1 Dec. 31, 2015

Related U.S. Application Data

(60) Provisional application No. 61/771,240, filed on Mar. 1, 2013.

(51) Int. Cl.
| | | |
|---|---|---|
| A61K 31/70 | (2006.01) | |
| C07H 21/02 | (2006.01) | |
| C07H 21/04 | (2006.01) | |
| C12N 15/115 | (2010.01) | |
| A61L 27/56 | (2006.01) | |
| A61L 27/54 | (2006.01) | |
| A61L 27/58 | (2006.01) | |
| A61K 31/711 | (2006.01) | |
| C12N 5/00 | (2006.01) | |
| C12Q 1/68 | (2006.01) | |

(52) U.S. Cl.
CPC ............ *C12N 15/115* (2013.01); *A61K 31/711* (2013.01); *A61L 27/54* (2013.01); *A61L 27/56* (2013.01); *A61L 27/58* (2013.01); *A61L 2300/258* (2013.01); *A61L 2430/00* (2013.01); *C12N 2310/16* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 4,739,044 | A | 4/1988 | Stabinsky |
| 4,757,141 | A | 7/1988 | Fung et al. |
| 5,270,163 | A | 12/1993 | Gold et al. |
| 5,466,468 | A | 11/1995 | Schneider et al. |
| 5,580,571 | A | 12/1996 | Hostetler |
| 5,626,869 | A | 5/1997 | Nyqvist et al. |
| 5,660,985 | A | 8/1997 | Pieken et al. |
| 6,818,395 | B1 | 11/2004 | Quake et al. |
| 7,169,560 | B2 | 1/2007 | Lapidus et al. |
| 7,282,337 | B1 | 10/2007 | Harris |
| 2002/0164629 | A1 | 11/2002 | Quake et al. |
| 2007/0212730 | A1 | 9/2007 | Vepari et al. |
| 2010/0034864 | A1 | 2/2010 | Spedden et al. |
| 2011/0104667 | A1 | 5/2011 | Gilman |

FOREIGN PATENT DOCUMENTS

WO   2012/068332 A2   5/2012

OTHER PUBLICATIONS

International Search Report and Written Opinion mailed on Aug. 25, 2014, for International Patent Application No. PCT/US14/19284, filed Feb. 28, 2014 (11 pages).

*Primary Examiner* — Sean McGarry
(74) *Attorney, Agent, or Firm* — Brown Rudnick LLP; Thomas C. Meyers

(57) ABSTRACT

The invention generally relates to aptamers that bind CD271. In certain aspects, the invention provides an isolated nucleic acid ligand that binds to CD271, in which the nucleic acid ligand includes the nucleotide sequence of SEQ ID NO: 1 or the nucleotide sequence of SEQ ID NO: 2.

6 Claims, 15 Drawing Sheets

*Randomer:* 5'-TAC GAC TCA CTA TAG GGA TCC-(N=28)-GAA TTC CCT TTA GTG AGG GTT-3' (SEQ ID NO: 3)
*Forward primer AP7:* TAC GAC TCA CTA TAG GGA TCC (SEQ ID NO: 4)
*Reverse primer AP3:* AAC CCT CAC TAA AGG GAA TT (SEQ ID NO: 5)

FIG. 6A

| | Sample | #base | Sequence |
|---|---|---|---|
| SEQ ID NO: 6 | A1 | 69 | Contains unknown nucleotides |
| SEQ ID NO: 7 | B1 | 70 | TACGACTCACTATAGGGATCCCCGCCCCCAGCCTCTCCGCGTTTTGAATTCCCTTTAGTGAGGGTT |
| SEQ ID NO: 8 | C1 | 70 | TACGACTCACTATAGGGATCCGGTGGGTAACGTCCGAGGGGCGTGTTGGAATTCCCTTTAGTGAGGGTT |
| SEQ ID NO: 9 | D1 | 70 | TACGACTCACTATAGGGATCCACGAAGGTAAACTAGGAAAAGCAGACGGAATTCCCTTTAGTGAGGGTT |
| SEQ ID NO: 10 | E1 | 70 | TACGACTCACTATAGGGATCCAAAAAAGCAAAAGCAAAAGAGTGTGAATTCCCTTTAGTGAGGGTT |
| SEQ ID NO: 11 | F1 | 70 | TACGACTCACTATAGGGATCCAGTAACTCCGGGAGACAATTGGAGGATGAATTCCTTTAGTGAGGGTT |
| SEQ ID NO: 12 | G1 | 69 | TACGACTCACTATAGGGATCCTGCAGTGGGGCCAGTTTTTTATCCGTGCGAATTCCTTTAGTGAGGGTT |
| SEQ ID NO: 13 | H1 | 70 | TACGACTCACTATAGGGATCCTATGTTTAATATATGCGGCACGGTGTGGGAATTCCCTTTAGTGAGGGTT |
| SEQ ID NO: 14 | A2 | 70 | TACGACTCACTATAGGGATCCAAAAGAACAATAAGTAGAGATGAAGAGTGAATTCCCTTTAGTGAGGGTT |
| SEQ ID NO: 15 | B2 | 70 | TACGACTCACTATAGGGATCCTTAATAAGTGGTGACGGAGAGATAGCGAGAATTCCCTTTAGTGAGGGTT |
| SEQ ID NO: 16 | C2 | 70 | TACGACTCACTATAGGGATCCATGTGCGTTTGTGTCGTGGGGAGGGTGAATTCCCTTTAGTGAGGGTT |
| SEQ ID NO: 17 | D2 | 70 | TACGACTCACTATAGGGATCCTTCGTTCTTCCGTGAATACGAAGATGCGGAATTCCCTTTAGTGAGGGTT |
| SEQ ID NO: 18 | E2 | 70 | TACGACTCACTATAGGGATCCAAGAAATTTACTGGCATAAGAATCTGACGAATTCCCTTTAGTGAGGGTT |
| SEQ ID NO: 19 | F2 | 70 | TACGACTCACTATAGGGATCCTAGCGAGAAGCAAACCGGGAGCAAACCGAATTCCGAATTCCCTTTAGTGAGGGTT |
| SEQ ID NO: 20 | G2 | 68 | Contains unknown nucleotides |
| SEQ ID NO: 21 | H2 | 70 | TACGACTCACTATAGGGATCCAATGGGCATTGGTTGAGATGTTCGGGAGAATTCCCTTTAGTGAGGGTT |
| SEQ ID NO: 22 | A3 | 70 | TACGACTCACTATAGGGATCCAATGCGAAAAAAAAGGCGGTAATTGAATTCCCTTTAGTGAGGGTT |
| SEQ ID NO: 23 | B3 | 70 | Contains unknown nucleotides |
| SEQ ID NO: 24 | C3 | 70 | TACGACTCACTATAGGGATCCATGGCGTAGAAGGCCGATGGAGTGACGGAGTGACGGAATTCCCTTTAGTGAGGGTT |
| SEQ ID NO: 25 | D3 | 70 | TACGACTCACTATAGGGATCCGAGTGAGTTGCTTGATTCGCCCGTAAGTGAATTCCTTTAGTGAGGGTT |
| SEQ ID NO: 26 | E3 | 70 | TACGACTCACTATAGGGATCCAAAAGAAAAAGCAGATTCAAAAATTTAGAATTCCCTTTAGTGAGGGTT |
| SEQ ID NO: 27 | F3 | 70 | TACGACTCACTATAGGGATCCAGACTAGACCAAGAGCCTACCCACAGAATTCCCTTTAGTGAGGGTT |
| SEQ ID NO: 28 | G3 | 70 | TACGACTCACTATAGGGATCCAAACAGTCATGTAAGGGGTGAGCACGAAGAATCCCTTTAGTGAGGGTT |

| | | | |
|---|---|---|---|
| | | | Contains unknown nucleotides |
| SEQ ID NO: 26 | H3 | 70 | TACGACTCACTATAGGGATCCAGCAAGTGCGCAGGATGAAACGTGTAGGAATTCCCTTTAGTGAGGGTT |
| SEQ ID NO: 27 | A4 | 70 | TACGACTCACTATAGGGATCCGGTGGGGGGGAAATTAGGGCAGGGGAATTCCCTTTAGTGAGGGTT |
| SEQ ID NO: 28 | B4 | 68 | TACGACTCACTATAGGGATCCCGTCTGCGGTCGGGGGTGGCGGCGGGTCAATTCCCTTTAGTGAGGGTT |
| SEQ ID NO: 29 | C4 | 70 | TACGACTCACTATAGGGATCCCCGCCCCACGCCTCTCCCGGCGTTTGGAATTCCCTTTAGTGAGGGTT |
| SEQ ID NO: 30 | D4 | 70 | TACGACTCACTATAGGGATCCAAGAAAAAGCCAAGATACAATCATGCGAGAATTCCCTTTAGTGAGGGTT |
| SEQ ID NO: 31 | E4 | 70 | TACGACTCACTATAGGGATCCGGTGGGCTGGTCGGGGTAATTGATCGAGAATTCCCTTTAGTGAGGGTT |
| SEQ ID NO: 32 | F4 | 70 | TACGACTCACTATAGGGATCCGCCGCGGTAGATATCACTTGGGAATTCCCTTTAGTGAGGGTT |
| SEQ ID NO: 33 | G4 | 70 | TACGACTCACTATAGGGATCCAGTTGGAGCAGCTTCTGGTCAGTGAATCGAATTCCCTTTAGTGAGGGTT |
| SEQ ID NO: 34 | H4 | 70 | TACGACTCACTATAGGGATCCGAGTGGGCTGCGAGTGGTTGGGGAGGAATTCCCTTTAGTGAGGGTT |
| SEQ ID NO: 35 | A5 | 70 | TACGACTCACTATAGGGATCCGGGAGACAGGAGGGGAAAGTATGTGGAATTCCTTTAGTGAGGGTT |
| SEQ ID NO: 36 | B5 | 70 | TACGACTCACTATAGGGATCCAAGCTTCAAAACAAAGACAACTAGGTGAGAATTCCCTTTAGTGAGGGTT |
| SEQ ID NO: 37 | C5 | 70 | TACGACTCACTATAGGGATCCACCATGAAAAGCAAAAGTTAGTCAGGTTCAGGTTGAATTCCCTTTAGTGAGGGTT |
| SEQ ID NO: 38 | D5 | 70 | TACGACTCACTATAGGGATCCAAGAGAGGGGAGCCAGAGACAGGGGAGAATTCCCTTTAGTGAGGGTT |
| SEQ ID NO: 39 | E5 | 70 | TACGACTCACTATAGGGATCCAAGCTTCAAAACAAAGACAACTAGGTGACAATTCCCTTTAGTGAGGGTT |
| SEQ ID NO: 40 | F5 | 70 | TACGACTCACTATAGGGATCCAAGAAGAAGAAGGGAGAGGGTGAAGGGTGAAGAGGGTGAATTCCCTTTAGTGAGGGTT |
| SEQ ID NO: 41 | G5 | 70 | TACGACTCACTATAGGGATCCAAAAGAAAAAAGATAAACTATGGAAGAGAATTCCCTTTAGTGAGGGTT |
| | H5 | 69 | |
| | | | Contains unknown nucleotides |
| SEQ ID NO: 42 | A6 | 70 | TACGACTCACTATAGGGATCCGCAAATACAAAAACGTATGCAGAGATAAGAATTCCCTTTAGTGAGGGTT |
| SEQ ID NO: 43 | B6 | 70 | TACGACTCACTATAGGGATCCTCCGATCAGTAAGCAAGAGAAATAAAGGAATTCCCTTTAGTGAGGGTT |
| SEQ ID NO: 44 | C6 | 70 | TACGACTCACTATAGGGATCCCCGGCAGACTAAGGCCGTACATGGGATCGAATTCCCTTAGTGAGGGTT |
| SEQ ID NO: 45 | D6 | 70 | TACGACTCACTATAGGGATCCATTATGAGGCGTGATGGCGGGGCTAAGGAATTCCCTTTAGTGAGGGTT |
| SEQ ID NO: 46 | E6 | 70 | TACGACTCACTATAGGGATCCGGTGGGGGGGGGGTGGGTTTTGGCTTGGGAATTCCCTTTAGTGAGGGTTT |
| SEQ ID NO: 47 | F6 | 70 | TACGACTCACTATAGGGATCCCTTGTTTGTTTCACCTGGTGGCCATATTTGAATTCCCTTTAGTGAGGGTT |
| | G6 | 70 | |
| | H6 | 69 | |
| | | | Contains unknown nucleotides |

| SEQ ID NO | Label | Sequence |
|---|---|---|
| SEQ ID NO: 48 | F2/1-70 | TACGACTCACTATAGGGATCCTAGCGGAAGCAAACCGGAGCAAACCGAATTCCCTTTAGTGAGGGTT |
| SEQ ID NO: 49 | G3/1-70 | TACGACTCACTATAGGGATCCCAAACAGTCATGTAAGGGTGAGGACGTAAGACGAATTCCCTTTAGTGAGGGTT |
| SEQ ID NO: 50 | H4/1-70 | TACGACTCACTATAGGGATCCAGTTGGAGCAGCATCTGGTCAGTGAATCGAATTCCCTTTAGTGAGGGTT |
| SEQ ID NO: 51 | A5/1-70 | TACGACTCACTATAGGGATCCGAGTGGGCTGCCGGAGGTGGTGGGAGGAATAGGAAAAGCAGACAGAGAATTCCCTTTAGTGAGGGTT |
| SEQ ID NO: 52 | D1/1-70 | TACGACTCACTATAGGGATCCCTTAATAAGTGGTGACGGAGATAGCGGAGAGAAACGTGTAGGGAATTCCCTTTAGTGAGGGTT |
| SEQ ID NO: 53 | B2/1-70 | TACGACTCACTATAGGGATCCAGCAAGTGCGCAGGATGAAAACGTGTAGGGAATTCGAGAATTCCCTTTAGTGAGGGTT |
| SEQ ID NO: 54 | A4/1-70 | TACGACTCACTATAGGGATCCAAAAAAAGCCACGATACAATCATGCGAGAATTCCCTTTAGTGAGGGTT |
| SEQ ID NO: 55 | E4/1-70 | TACGACTCACTATAGGGATCCAAAAAACCAAGACCACAAGAGTGTAAGAGTGTAAGAGAATTCCCTTTAGTGAGGGTT |
| SEQ ID NO: 56 | E1/1-70 | TACGACTCACTATAGGGATCCAAAAAGCAGATTCAAAAATTAGAATTGAATTCCCTTTAGTGAGGGTT |
| SEQ ID NO: 57 | E3/1-70 | TACGACTCACTATAGGGATCCAAAAGCGAAAAAAAAAAGGCGGTAATTGAATTCCCTTTAGTGAGGGTT |
| SEQ ID NO: 58 | A3/1-70 | TACGACTCACTATAGGGATCCAAGCTTCAAAAACAAAGATAAACTATGGAAGAGAATTCCCTTTAGTGAGGGTT |
| SEQ ID NO: 59 | H5/1-70 | TACGACTCACTATAGGGATCCAAGCTTCAAAACAAAGACAAACAAGTTAGTCAGGTTGAATTCCCTTTAGTGAGGGTT |
| SEQ ID NO: 60 | D5/1-70 | TACGACTCACTATAGGGATCCAAGCTTCAAAAGACAAGACAACTAGGTGGGAATTCCCTTTAGTGAGGGTT |
| SEQ ID NO: 61 | C5/1-70 | TACGACTCACTATAGGGATCCAAGACTAGAACCAAGAGCCTACCCACAGAATTCCCTTTAGTGAGGGTT |
| SEQ ID NO: 62 | F5/1-70 | TACGACTCACTATAGGGATCCCGGTGGGTAAGGACCGTGTTGGAATTCCCTTTAGTGAGGGTT |
| SEQ ID NO: 63 | F3/1-70 | TACGACTCACTATAGGGATCCAATGGGGCCATTGGTTGTTGAGATGTTCGGAGAATTCCCTTTAGTGAGGGTT |
| SEQ ID NO: 64 | C1/1-70 | TACGACTCACTATAGGGATCCGGTGGGCTGGTCGGGGTTGATCGGGGGAATTCCCTTTAGTGAGGGTT |
| SEQ ID NO: 65 | H2/1-70 | TACGACTCACTATAGGGATCCGGTGGGCTCTTGCCGGTACGGCGGGTGGGCGTAAGTGAATTCGAATTCCCTTTAGTGAGGGTT |
| SEQ ID NO: 66 | F4/1-70 | TACGACTCACTATAGGGATCCGGTGGGCTCTTGCCGGTACGGGGCCCGTAAGTGAATTGAATTCCCTTTAGTGAGGGTT |
| SEQ ID NO: 67 | F6/1-70 | TACGACTCACTATAGGGATCCGAGTGAGTTGCTTGATTCGCCCGTAAGTGAATGAATATTTGAATTCCCTTTAGTGAGGGTT |
| SEQ ID NO: 68 | C4/1-70 | TACGACTCACTATAGGGATCCGAGTTGCTTGATTCGCCCGTAAGTGAATATTTGAATTCCCTTTAGTGAGGGTT |
| SEQ ID NO: 69 | D3/1-70 | TACGACTCACTATAGGGATCCTTGTTTGTTTCACCTGGTCGCCATATTTGCGTGCGAATTTGAATTCCCTTTAGTGAGGGTT |
| SEQ ID NO: 70 | G6/1-70 | TACGACTCACTATAGGGATCCTTGTTTGTTTCACCTGGTCGCCATATTTGAATTCCCTTTAGTGAGGGTT |

FIG. 8A

| SeqA | Name | Len (nt) | SeqB | Name | Len (nt) | Score |
|---|---|---|---|---|---|---|
| 1 | B1 | 70 | 22 | D4 | 70 | 100 |
| 29 | C5 | 70 | 32 | F5 | 70 | 100 |
| 33 | G5 | 70 | 41 | MOTIF | 70 | 90 |
| 31 | E5 | 70 | 41 | MOTIF | 70 | 82.8571 |
| 14 | A3 | 70 | 34 | H5 | 70 | 81.4286 |
| 3 | D1 | 70 | 41 | MOTIF | 70 | 80 |
| 31 | E5 | 70 | 33 | G5 | 70 | 80 |
| 34 | H5 | 70 | 41 | MOTIF | 70 | 80 |
| 4 | E1 | 70 | 33 | G5 | 70 | 78.5714 |
| 14 | A3 | 70 | 33 | G5 | 70 | 78.5714 |
| 24 | F4 | 70 | 39 | F6 | 70 | 78.5714 |
| 27 | A5 | 70 | 41 | MOTIF | 70 | 78.5714 |
| 4 | E1 | 70 | 17 | E3 | 70 | 77.1429 |
| 5 | F1 | 70 | 33 | G5 | 70 | 77.1429 |
| 5 | F1 | 70 | 41 | MOTIF | 70 | 77.1429 |
| 14 | A3 | 70 | 30 | D5 | 70 | 77.1429 |
| 20 | A4 | 70 | 23 | E4 | 70 | 77.1429 |
| 21 | C4 | 70 | 24 | F4 | 70 | 77.1429 |
| 21 | C4 | 70 | 39 | F6 | 70 | 77.1429 |
| 29 | C5 | 70 | 41 | MOTIF | 70 | 77.1429 |
| 32 | F5 | 70 | 41 | MOTIF | 70 | 77.1429 |
| 33 | G5 | 70 | 34 | H5 | 70 | 77.1429 |
| 4 | E1 | 70 | 23 | E4 | 70 | 75.7143 |
| 7 | A2 | 70 | 35 | B6 | 70 | 75.7143 |
| 11 | E2 | 70 | 28 | B5 | 70 | 75.7143 |
| 11 | E2 | 70 | 41 | MOTIF | 70 | 75.7143 |
| 14 | A3 | 70 | 41 | MOTIF | 70 | 75.7143 |
| 20 | A4 | 70 | 41 | MOTIF | 70 | 75.7143 |
| 2 | C1 | 70 | 39 | F6 | 70 | 74.2857 |
| 3 | D1 | 70 | 33 | G5 | 70 | 74.2857 |

| 4 | E1 | 70 | 14 | A3 | 70 | 74.2857 |
| 7 | A2 | 70 | 13 | H2 | 70 | 74.2857 |
| 7 | A2 | 70 | 23 | E4 | 70 | 74.2857 |
| 9 | C2 | 70 | 33 | G5 | 70 | 74.2857 |
| 10 | D2 | 70 | 11 | E2 | 70 | 74.2857 |
| 15 | C3 | 70 | 28 | B5 | 70 | 74.2857 |
| 16 | D3 | 70 | 40 | G6 | 70 | 74.2857 |
| 18 | F3 | 70 | 29 | C5 | 70 | 74.2857 |
| 18 | F3 | 70 | 32 | F5 | 70 | 74.2857 |
| 21 | C4 | 70 | 31 | E5 | 70 | 74.2857 |
| 24 | F4 | 70 | 28 | B5 | 70 | 74.2857 |
| 26 | H4 | 70 | 27 | A5 | 70 | 74.2857 |
| 27 | A5 | 70 | 31 | E5 | 70 | 74.2857 |
| 28 | B5 | 70 | 31 | E5 | 70 | 74.2857 |
| 28 | B5 | 70 | 41 | MOTIF | 70 | 74.2857 |
| 1 | B1 | 70 | 25 | G4 | 70 | 72.8571 |
| 3 | D1 | 70 | 11 | E2 | 70 | 72.8571 |
| 4 | E1 | 70 | 29 | C5 | 70 | 72.8571 |

FIG. 8B

APTAMERS THAT BIND CD271

RELATED APPLICATION

The present application is a 35 U.S.C. §371 national phase application of PCT international application number PCT/US 14/19284, filed Feb. 28, 2014, which claims the benefit of and priority to U.S. provisional patent application Ser. No. 61/771,240, filed Mar. 1, 2013, the content of each of which is incorporated by reference herein in its entirety.

GOVERNMENT SUPPORT

This invention was made with government support under W81XWH-10-C-0160 awarded by the United States Army. The government has certain rights in the invention.

FIELD OF THE INVENTION

The invention generally relates to aptamers that bind CD271.

SEQUENCE LISTING

The instant application contains a Sequence Listing which has been submitted in ASCII format via EFS-Web and is hereby incorporated by reference in its entirety. Said ASCII copy, created on Oct. 2, 2014, is named VIVO_003_01US sequence listing ST25.txt and is 24 kilobytes in size.

BACKGROUND

CD271 (LNGFR) is a transmembrane protein that is a member of the Tumor Necrosis Factor receptor (TNFR) super family of transmembrane proteins. CD271 is widely expressed in developing neural tissue. In mature cells, expression is found in adult stem cells, endothelial cells, perivascular fibroblasts, dental pulp cells, prostate epithelial cells and immune B cells.

Importantly, although CD271 is abundantly expressed during development, it is down regulated in many cells of the adult organism. It has been found that CD271 is overexpressed in various types of cancer. For example, it has been found that CD271 is a useful marker in specific non-neural mesenchymal tumors such as dermatofibrosarcoma and rhadomyosarcoma, in skin cancers such as melanoma, and in breast cancer.

SUMMARY

The invention recognizes that targeting CD271 is useful for drug delivery for treating certain cancers and for recruitment of adult stem cells in vivo for tissue regeneration. Accordingly, the invention provides aptamers that specifically bind CD271. The aptamers can have a drug linked to them to allow for targeted treatment of cancers in which CD271 is overexpressed. Additionally, the aptamers can be linked to an implantable medical product that includes a scaffold to facilitate recruitment of adult stem cells to the scaffold, resulting in an increased rate of tissue regeneration around the scaffold.

Certain aspects of the invention provide isolated nucleic acid ligands that binds to CD271. The nucleic acid ligands of the invention include the nucleotide sequence of SEQ ID NO: 1 or the nucleotide sequence of SEQ ID NO: 2. The nucleic acid ligands may be single stranded or double stranded. The nucleic acid ligands may be DNA or RNA. In other embodiments, the nucleic acid ligands include an RNA sequence transcribed from a nucleotide sequence selected from the group consisting of SEQ ID NO: 1 and SEQ ID NO: 2.

The nucleic acid ligands may be linked to other molecules. The linkage may be by any method known in the art. The linkage may be a cleavable linkage. For example, nucleic acid ligands of the invention may be linked to a detectable label, such as an optically detectable label, such as a fluorescent label. In other embodiments, nucleic acid ligands of the invention may be linked to a drug, such as an anti-cancer drug or an antioxidant.

Linkage of aptamers of the invention to a drug allows for targeted delivery to cells that express CD271, such as cancer cells. In certain embodiments, the CD271 specific aptamers can be bound to the surface of drug nano-carriers and will serve as ligands capable of attaching nano-scale drug carriers (e.g., lyposomes and polymersomes) to the targeted cells. As the high affinity aptamers bind tightly to the cellular surfaces expressing CD271, the probability of internalization of decorated nanocarriers by the treated cells increases. That results in a higher rate of delivery of the desired drugs into the targeted cells. Increasing delivery rate can potentiate the clinical effects caused by the formulated drugs for a dose of administered drug. It can also create an opportunity to decrease the administered dose. In a similar manner, CD271-specific aptamers can be coupled (e.g., covalently or non-covalently) to a drug and can be used for delivery of the drugs inside the targeted cells.

Another aspect of the invention provides an implantable medical product. The product includes a scaffold composed of a biocompatible material, and a plurality of nucleic acid ligands that binds to CD271. The nucleic acid ligands may include the nucleotide sequence of SEQ ID NO: 1 or the nucleotide sequence of SEQ ID NO: 2. Once implanted, the aptamers will attach adult stem cells that express CD271, such as mesenchymal stem cells. The increased rate of adult stem cell retention results in increased density of somatic tissue cells generated on the surface of the implant, providing an increased rate of tissue regeneration.

Any scaffold known in the art may be used. The scaffold may be porous or non-porous. The nucleic acid ligands may be coupled to an external surface of the scaffold. When porous, the ligands may be coupled to either or both an internal or external surface of the scaffold. The scaffold may also be bioresorbable.

Another aspect of the invention provides isolated nucleotide sequences including SEQ ID NO: 1 or SEQ ID NO: 2, or nucleotide sequences substantially identical thereto. The nucleotide sequences of the invention may further include a detectable label, such as a fluorescent label. The isolated nucleotide sequences may bind to CD271.

Certain embodiments provide a polypeptide encoded by a nucleotide sequence including SEQ ID NO: 1, SEQ ID NO: 2, or nucleotide sequences substantially identical thereto. The invention also provides a vector include a nucleotide sequence having SEQ ID NO: 1, SEQ ID NO: 2, or nucleotide sequences substantially identical thereto, operably linked to an expression control element. The invention also provides isolated host cells transformed with a vector including a nucleotide sequence having SEQ ID NO: 1, SEQ ID NO: 2, or nucleotide sequences substantially identical thereto. Certain embodiments provide an isolated nucleotide sequence that hybridizes to a nucleotide sequence having SEQ ID NO: 1, SEQ ID NO: 2, or nucleotide sequences substantially identical thereto under high stringency conditions. Other embodiments provide an isolated nucleotide sequence that is complementary to a nucleotide sequence having SEQ ID NO: 1, SEQ ID NO: 2, or nucleotide sequences substantially identical thereto.

BRIEF DESCRIPTION OF THE DRAWINGS

FIGS. 6A-B shows the sequences of cloned aptamers.

FIGS. 7A-B shows the multiple alignments of sequenced MSCs aptamers. The selected motif for aptamer pool (1391-Motif).

FIGS. 8A-B shows the similarity scores of the sequenced aptamers.

DETAILED DESCRIPTION

Figure 1:
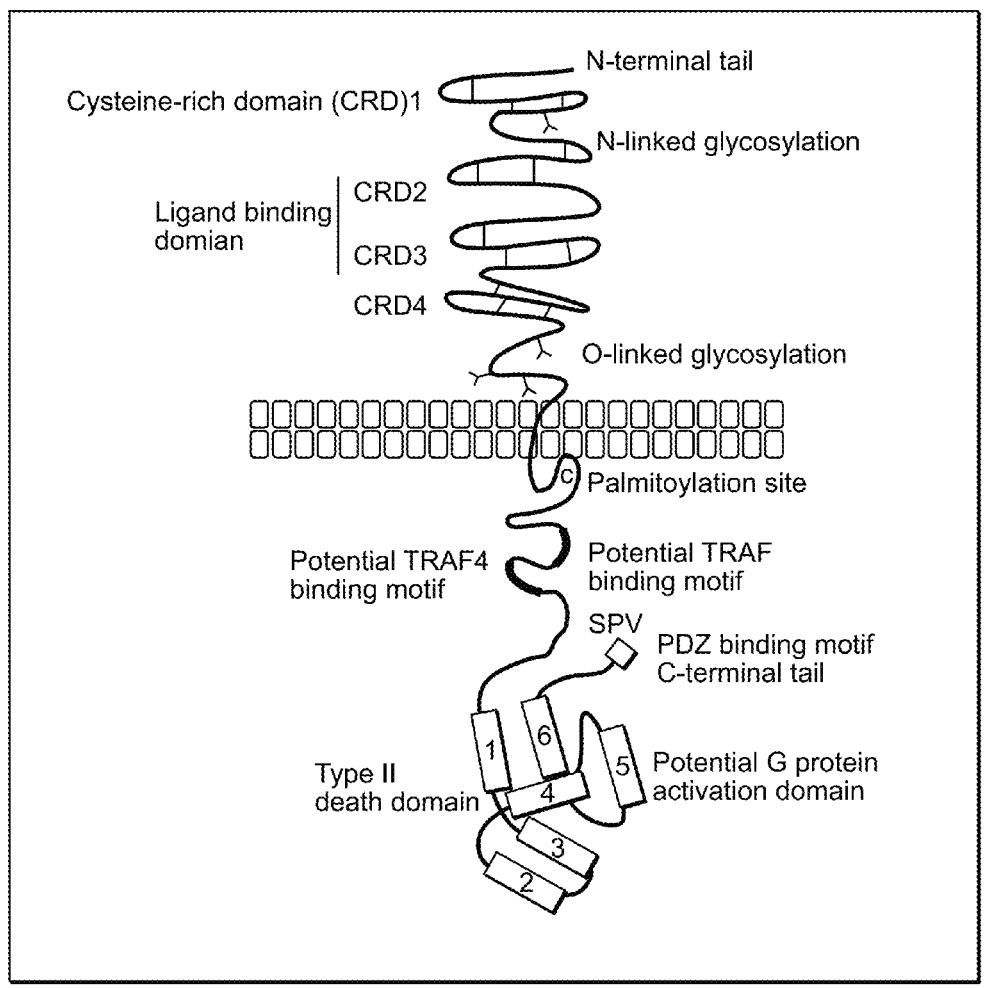
FIG. 1 is a schematic representation of the structure of the CD271 protein. CD271 is a Type I transmembrane receptor with an extracellular domain that contains four cysteine-rich domains (CRDs), and one N- and several O-linked glycosylation sites. The intracellular domain contains a palmitoylation site at cysteine 279, two potential TRAF-binding sites, a Type II death domain, a potential G protein activating domain, and a PDZ domain binding motif.

The invention generally relates to aptamers that bind CD271. The invention recognizes that targeting CD271 is useful for histological applications involving visualization of cells and tissues expressing CD271, delivery of drugs into cells and tissues expressing CD271 (e.g., for treating certain cancers), and for recruitment of adult stem cells in vivo for tissue regeneration. Aptamers of the invention may also be used for interference/competition with the binding of natural CD271 ligands to CD271, thus enabling control of cellular signaling. That ability has numerous potential therapeutic applications, such as, for example, pain reduction. In certain embodiments, it is envisioned that a pain drug, such as Pfizer's Tanezumab, would be capable of binding to and reducing the concentration of nerve growth factor (NGF).

Aptamers

A nucleic acid ligand, also known as an aptamer, is a nucleic acid macromolecule (e.g., DNA or RNA) that binds tightly to a specific molecular target Like all nucleic acids, a particular nucleic acid ligand may be described by a linear sequence of nucleotides (A, U, T, C and G), typically 15-40 nucleotides long, however aptamers have little or no sequence identity recognized by the nucleic acid binding proteins in nature and instead rely upon a defined three-dimensional structure. Binding of a nucleic acid ligand to a target molecule is not determined by nucleic acid base pairing, but by the three-dimensional structure of the aptamer. See, for example, Jayasena, Clin. Chem. 45(9):1628-1650, 1999 and Baldrich et al., Anal. Chem. 2004; 76(23):7053-7063. In solution, the chain of nucleotides forms intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the femtomolar to low nanomolar range.

The high affinity properties of aptamers can be determined by an iterative process known as SELEX (Systematic Evolution of Ligands by Exponential enrichment), whereby through negative selection, a particular aptamer can be selected for a particular target molecule. Once identified, the aptamer can be chemically modified for inclusion of additional properties. For example, aptamers can be modified to bind or link to a structure, molecule, nanoparticle, etc.

The aptamers of the invention specifically bind CD271. The nucleic acid ligands of the invention include the nucleotide sequence of SEQ ID NO: 1 or the nucleotide sequence of SEQ ID NO: 2. The nucleic acid ligands may be single stranded or double stranded. The nucleic acid ligands may be DNA or RNA. In other embodiments, the nucleic acid ligands include an RNA sequence transcribed from a nucleotide sequence selected from the group consisting of SEQ ID NO: 1 and SEQ ID NO: 2.

CD271

CD271, (or p75NTR) is the sixteenth member of the Tumor Necrosis Factor receptor (TNFR) super family of transmembrane proteins. Members of the TNFR family including CD271, share homology in their extracellular domain, and have a cytoplasmic death domain. CD271 has unique intracellular structure and downstream signaling partners. CD271 is also differentiated from other members of the TNFR receptor family in that it binds pro and mature neurotrophins and affects the growth, differentiation and death of the nervous system. The ligands for CD271 are neurotrophins, which are Nerve Growth Factor (NGF), Brain-Derived Growth factor (BDNF), Neurotrophin 3 (NT3) and Neurotrophin 4/5 (NT4/5). CD271 (LNGFR) is expressed on mesenchymal stem/stromal cells (MSCs); follicular dendritic cells; mesenchymal cells involved in mesenchymal-epithelial interactions; autonomic and sensory neurons; oligodendrocytes; astrocytes; schwann cells; and neural crest stem cells.

After cleavage of its 28-amino acid signal peptide, CD271 is a 399-amino acid transmembrane protein that has a single asparagine-linked carbohydrate at position 33 and several O-linked carbohydrates in the juxtamembrane stalk domain (FIG. 1). Like all members of the TNFR superfamily, CD271 contains cysteine-rich domains (CRD) in the extracellular domain. There are four CRDs (CRD1-CRD4 from amino-terminus) in CD271. Experimental and structural modeling studies have mapped the neurotrophin binding sites to CRD2 and CRD3. Cysteine 279 of the intracellular domain of p75NTR is palmitoylated and multiple serine and threonine residues are phosphorylated in the mature protein. The functions of these post-translational modifications are not known but could include roles in protein-protein interaction, proper intracellular folding of the receptor, or in directing the cellular localization of CD271. Both alternative splicing and post-synthetic proteolysis result in production of various truncated isoforms of CD271, including the neurotrophin receptor homologue 2 (NRH2) which has been found to associate with the other major receptor for NGF, the Tyrosine Kinase A receptor (TrkA) and bind NGF.

CD271 is an unusual member of the TNFR family due to its propensity to bind dimeric rather than trimeric ligands, and because the neurotrophins are structurally unrelated to the ligands which typically bind TNFR family members. However, in keeping with its membership in the TNFR family, the intracellular domain of CD271 contains an 80-amino acid 'death domain' module with six a helices, similar to TNFR1. However, unlike TNFR1, CD271 contains TRAF-interacting motifs which classify it as a Type II death domain, and activation of these leads to multiple signal transduction pathways. CD271 is further described in Rogers et al. (Journal of Biological Regulators & Homeostatic Agents, 2(1):1-6, 2008), the content of which is incorporated by reference herein in its entirety.

Selection of Aptamers

Nucleic acid ligands of the invention can be identified using any methods known in the art, such as SELEX as described in Gold et al. (U.S. Pat. No. 5,270,163), the content of which is incorporated by reference herein in its entirety. Other nucleic acid ligand identification methods are shown in Gilman et al. (U.S. patent application number 2011/0104667), the content of which is incorporated by reference herein in its entirety. Identification of aptamers of the invention is shown in the Examples below.

SELEX is a strategy developed for the identification of nucleic acids that can bind target molecules with high affinity and specificity through their three-dimensional conformation. The technique involves identification of rare nucleic acid molecules that have high affinity for a target molecule from a pool of random nucleic acids. The process is completed iteratively, with subsequent repeated rounds of selection and amplification. This procedure has proved to be extremely useful for the isolation of tight-binding oligonucleotide ligands (aptamers) for a number of target molecules, such as nucleic acid-binding proteins, non-nucleic acid-binding proteins, and certain small molecules. SELEX is an efficient screening method because iterative cycles of selection can be carried out using Polymerase Chain Reaction (PCR).

The SELEX process generally involves defining a target molecule, such as a protein, a small molecule, or a supramolecular structure. A library of random oligonucleotides (~1× 1015 oligonucleotides) is created. The random pool of DNA generally has primer binding sites at the end of each oligonucleotide to provide an efficient way to find and PCR amplify oligonucleotides that bind to the target molecule. The target molecule is exposed to the oligonucleotide "library" and a few of these oligonucleotides in the library will bind to the target, thus defining the target specific aptamers. The non-binding oligonucleotides are separated from the binding oligonucleotides.

Aptamer identification methods described in Gilman involve single step separation of nucleic acids that bind the target molecule with the greatest affinity from nucleic acids that bind the target molecule with a lesser affinity and nucleic acids that do not bind the target molecule, thereby identifying the nucleic acid ligand of the target molecule. The selective separation protocols generate conditions in which the nucleic acids that bind the target molecule with a lesser affinity and nucleic acids that do not bind the target molecule cannot form complexes with the target molecule or can only form complexes with the target molecule for a short period of time. In contrast, the conditions of the separation protocols allow nucleic acids that bind the target molecule with greatest affinity to form complexes with the target molecule and/or bind the target molecule for the greatest period of time, thereby separating in a single step the nucleic acids with the greatest affinity for the target molecule, i.e., the nucleic acid ligands, from the remaining nucleic acids in the candidate mixture.

Separating can be accomplished by any of numerous methods that provide for selective single step separation of nucleic acids that bind the target molecule with greatest affinity from nucleic acids that bind the target molecule with a lesser affinity and nucleic acids that do not bind the target molecule. Exemplary separating procedures include HPLC gradient elution and gel electrophoresis.

After incubation, the mixture is washed with buffer to remove unbound target molecules. The beads having bound target molecules are then incubated with the candidate mixture of nucleic acids. The beads having bound target molecules can be loaded into an HPLC column prior to incubating with the candidate mixture. If the beads having bound target molecules are loaded into the HPLC column prior to incubation with the candidate mixture, incubating of the candidate mixture and the target molecule occurs on the column.

After the candidate mixture has been incubated with the target molecules bound to the beads for sufficient time that bead/target molecule/nucleic acid complexes can form, an HPLC elution gradient is applied to the column in order to obtain the nucleic acid ligands of the target molecule. During the elution process the effluent will be enriched in nucleic acid ligands of higher affinity for the target molecule, and eventually the final fractions contain the nucleic acid ligands of the highest affinity to the target molecule.

Sequencing

After identification, the nucleic acid ligands of the invention may be sequenced. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing may be by any method known in the art. See for example Sanger et al. (Proc Natl Acad Sci USA, 74(12): 5463 67, 1977), Maxam et al. (Proc. Natl. Acad. Sci., 74: 560-564, 1977), and Drmanac, et al. (Nature Biotech., 16:54-58, 1998), which references describe exemplary conventional ensemble sequencing techniques. Also see Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., (PNAS (USA), 100: 3960-3964, 2003), which references describe exemplary single molecule sequencing by synthesis techniques. The contents of each of these references is incorporated by reference herein in its entirety.

Aptamer Modification

In aspects of the invention, the CD271 specific aptamers may comprise at least one chemical modification. See for example, Wang et al., "Improving the stability of aptamers by chemical modification," Curr. Med. Chem., 2011; 18(27): 4126-38, and Kusser, Rev. Molecular Biotechnology, volume 74, issue 1, 1 Mar. 2000, Pages 27-38, "Chemically modified nucleic acid aptamers for in vitro selections: evolving evolution," each describing methods of chemically modifying aptamers. Modification can include a chemical substitution at a sugar position, a chemical substitution at an internucleotide linkage or a chemical substitution at a base position. Modification can also include incorporation of a modified nucleotide; a 3' cap; a 5' cap; or modification can include conjugation to a non-immunogenic compound, or to a lipophilic compound. A common modification is the incorporation of polyethylene glycol, or in some embodiments, polyethylene glycol is methoxypolyethylene glycol (mPEG).

It should be appreciated that the aptamers of the invention may be modified for the variety of applications discussed herein. Certain chemical modifications of the nucleic acid ligands of the invention may be made to increase the in vivo stability of the nucleic acid ligand or to enhance or to mediate the delivery of the nucleic acid ligand. See, e.g., Pieken et al. (U.S. Pat. No. 5,660,985), the content of which is incorporated by reference herein in its entirety. Modifications of the nucleic acid ligands contemplated in this invention include, but are not limited to, those that provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to 2-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In certain embodiments of the instant invention, the nucleic acid ligands are RNA molecules that are 2'-fluoro (2'-F) modified on the sugar moiety of pyrimidine residues.

In some embodiments, aptamers of the invention may be coupled to a drug, via a binding pair, or other attachment strategies known in the art. The methods of attaching labels to the ligands may be used to attach the drug to the ligand. The aptamer may be chemically modified to allow for conjugation, as discussed below. It should be appreciated that any modification technique can be employed to selectively conjugate to a molecule, particle, or device.

Conjugation of aptamers to drug molecules for targeted drug delivery can be accomplished by known techniques. See for example Yu-Fen et al., "Moleculare Assembly of an Aptamer-Drug Conjugate for Targeted Drug Delivery to Tumor Cells," ChemBioChem, volume 10, issue 5, pages 862-868, Mar. 23, 2009, which discusses covalent conjugation of drug and aptamer complexes. See also Bagalkot et al., "An Aptamer-Doxorubicin Physical Conjugate as a Novel Targeted Drug-Delivery Platform," Angewandte Chemie International Edition, volume 45, issue 48, pages 8149-8152, Dec. 11, 2006, which discusses a physical conjugate between doxorubicin and an aptamer. See also, Lee et al. "Molecular diagnostic and drug delivery agents based on aptamer-nanomaterial conjugates," Adv. Drug Delivery Reviews, vol. 62, issue 6, 30 Apr. 2010, pages 592-606, which discusses methods of integration. The references are hereby incorporated by reference.

In some embodiments of the invention, the aptamers are conjugated to liposome or other vehicles for targeted drug delivery. For example, in drug delivery methods discussed below, therapeutic agents can be encapsulated within a liposome and then conjugated to an aptamer by known methods. See for example Angew. Chem. Int. Ed. 2009, 48, 6494-6498, "Reversible Cell-Specific Drug Delivery with Aptamer-Functionalized Liposomes," where an aptamer is conjugated to a liposome by inserting the cholesterol tag onto the aptamer and immobilizes the aptamer on the surface by inserting into the hydrophobic lipid membrane. See also Mann et al., Oncotarget. 2011 April; 2(4): 298-304, "Thioaptamer Conjugated Liposomes for Tumor Vasculature Targeting," discussing long circulating liposomes with the outer surface decorated with thioated oligonucleotide aptamer (thioaptamer). Employing such techniques, the CD271 specific aptamers of the invention conjugated to a liposomal delivery vesicle can provide targeted delivery of therapeutic agents to cells expressing CD271. In some aspects of the invention, the aptamers may be connected to one or more PEG moieties, with or without one or more linkers. The PEG moieties may be any type of PEG moiety (linear, branched, multiple branched, star shaped, comb shaped or a dendrimer), or at any molecular weight. The same or different linkers or no linkers may be used to connect the same or different PEG moieties to an aptamer. Commonly known linkers include, but are not limited to, amines, thiols and azides, and can include a phosphate group.

Nucleic acid ligands of the invention can further include a nucleotide analog. Exemplary nucleotide analogs include xanthine or hypoxanthine, 5-bromouracil, 2-aminopurine, deoxyinosine, or methylated cytosine, such as 5-methylcytosine, N4-methoxydeoxycytosine, and the like. Also included are bases of polynucleotide mimetics, such as methylated nucleic acids, e.g., 2'-O-methRNA, peptide nucleic acids, locked nucleic acids, modified peptide nucleic acids, and any other structural moiety that acts substantially like a nucleotide or base, for example, by exhibiting base-complementarity with one or more bases that occur in DNA or RNA.

The nucleic acid ligands may further include a detectable label, such as radioactive labels, chemoluminescent labels, luminescent labels, phosphorescent labels, fluorescence polarization labels, and charge labels. In certain embodiments, the detectable label is a fluorescent label. Suitable fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescently labeled nucleotides may be obtained commercially (e.g., from NEN DuPont, Amersham, and BDL). Alternatively, fluorescently labeled nucleotides may also be produced by various techniques, such as those described in Kambara et al. (Bio/Technol., 6:816-21, 1988); Smith et al. (Nucl. Acid Res., 13:2399-2412, 1985); and Smith et al. (Nature, 321: 674-679, 1986). The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach (IRL Press, Oxford, 1991); Zuckerman et al. (Polynucleotides Res., 15: 5305-5321, 1987); Sharma et al. (Polynucleotides Res., 19:3019, 1991); Giusti et al. (PCR Methods and Applications, 2:223-227, 1993); Fung et al. (U.S. Pat. No. 4,757,141); Stabinsky (U.S. Pat. No. 4,739, 044); Agrawal et al. (Tetrahedron Letters, 31:1543-1546, 1990); Sproat et al. (Polynucleotides Res., 15:4837, 1987); and Nelson et al. (Polynucleotides Res., 17:7187-7194, 1989). Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra.

Therapeutic Applications

In certain aspects of the invention, aptamers of the invention are used for targeted delivery of drugs to tissue or cells that express CD271. Importantly, although CD271 is abundantly expressed during development, it is down regulated in many cells of the adult organism and only re-expressed in conditions involving neuronal injury, such as neurodegenerative disease states. Numerous neurological diseases, deficits and syndromes have been correlated with CD271 expression. These include Alzheimer's disease, amyotrophic lateral sclerosis, neural crest tumors, stroke, ischemia and excitotoxicity, cerebellar Purkinje cell degeneration, schizophrenia, bronchial asthma and some autoimmune disorders. The expression patterns of CD271 is associated with various types of cancer, such as non neural mesenchymal tumours (dermatofibrosarcoma and rhadomyosarcom). In addition, in some cancers such as prostate and bladder carcinoma, CD271 acts as a tumor suppressor and progression from benign to metastatic tumors is associated with a decrease in CD271 expression.

Incorporation of the aptamer into a drug delivery system provides for a targeted therapeutic response. For example, CD271 is a marker of the cancer stem cell-like population in human melanoma tissues. See Furuta et al. "CD271 on Melanoma Cell Is an IFN-γ-Inducible Immunosuppressive Factor that Mediates Downregulation of Melanoma Antigens," Journal of Investigative Dermatology (13 Nov. 2013). Therefore, a complex of an aptamer of the invention coupled to a chemotherapeutic drug can be used for targeted delivery of the chemotherapeutic agent to human melanoma tissues that expresses CD271.

In another application of the invention, aptamers conjugated to a therapeutic agent can be targeted to CD271 cells associated with pancreatic cancer. CD271 expression is found pancreatic stellate cells around pancreatic tumors (not in the center of the tumors). In addition, CD271 expression arises at the early stage of pancreatic carcinogenesis and CD271 expression is significantly correlated with a better prognosis in patients. See Fufiwara et al., "$CD271^+$ subpopulation of pancreatic stellate cells correlates with prognosis of pancreatic cancer and is regulated by interaction with cancer cells," PLoS One, 2012; 7(12):e52682. doi: 10.1371/journal.pone.0052682, Epub 2012 Dec. 27. The expression of CD271 on the outer boundary of pancreatic tumors provides for a localized target for binding aptamers of the invention to deliver therapeutic agents. In addition, detection of CD271 in pancreatic cancers can provide diagnostic information for treatment protocol selection.

In another embodiment, the CD271 specific aptamers of the invention are used in treatment of Nerve Growth factor (NGF) based diseases, such as Alzheimer's, chronic pain, Parkinson's disease, diabetes, ischemia, etc. by providing a mechanism to deliver NGF to localized regions in an organism. NGF is a small secreted protein that is important for the growth, maintenance, and survival of certain target neurons (nerve cells). NGF can function as a signaling molecule and can bind to CD271. For example, in the CNS, NGF also regulates phenotypic features in noradrenergic nuclei of hypothalamus and brainstem, participating in the central regulation of autonomic response and in the modulation of stress axis activity. NGF plays a pivotal role in the survival and function of cholinergic neurons of the basal forebrain complex, such functions include attention, arousal, motivation, memory and consciousness. The action of NGF on cholinergic neurons of the basal forebrain and on sensory neurons in dorsal root ganglia makes it a candidate for clinical use in Alzheimer's disease patients and in peripheral neuropathies respectively. For example, the aptamers of the invention can encapsulate a plurality of NGF molecules for localized delivery of NGF molecules, such as in a liposome or other vehicle delivery system.

In some embodiments of the invention, the neurological disorders can be treated with NGF. Since basal forebrain complex neurons are highly affected in Alzheimer's disease, NGF has been indicated as a potential protective and/or curative factor for neurodegenerative disorders associated with these neurons.

NGF is associated with many afflictions and conditions, where the present invention can be used in the regulation of NGF binding to CD271. It has also been demonstrated that NGF could directly act on two classical hallmark of Alzheimer's disease: β-amyloid neurotoxicity and tau hyperphosphorylation. See Scott S A, Mufson E J, Weingartner J A, Skau K A, Crutcher K A: Nerve growth factor in Alzheimer's disease: increased levels throughout the brain coupled with declines in nucleus basalis, J Neurosci 1995, 15:6213-6221. Indeed in vitro and in vivo experiments indicated NGF as a direct anti-amyloidogenic factor, being able to regulate both amyloid gene expression and protein processing. Furthermore NGF has been shown to counteract tau hyperphosphorylation both in vitro and in vivo. Further studies on human tissues failed to demonstrate a reduction of NGF production in the cortex and hippocampus of Alzheimer's disease patients, while the evidence for a decreased NGF immunoreactivity in the BFC suggested that impaired NGF supply via retrograde transport could be the effective cause of cholinergic neurodegeneration in Alzheimers. In addition to Alzheimers' NGF is known to impact Parkinson's disease, and therefore, the present invention could be implemented as a treatment or diagnostic tool. See Olson L, Backlund E O, Ebendal T, Freedman R, Hamberger B, Hansson P, Hoffer B, Lindblom U, Meyerson B, Stromberg I, et al.: Intraputaminal infusion of nerve growth factor to support adrenal medullary autografts in Parkinson's disease. One-year follow-up of first clinical trial, Arch Neurol 1991, 48:373-381.

In an aspect of the invention, the CD271 specific aptamers of the invention can interfere or compete with NGF binding. For example, the CD271 specific aptamers of the invention are introduced into an organism and bind to CD271, therefore blocking the binding of NGF, BDNF, NT-3, and NT-4. The neurotrophins that bind to the LNGFR, or CD271, comprise Nerve Growth Factor (NGF), Brain Derived Neurotrophic Factor (BDNF), Neurotrophin-3 (NT-3), and Neurotrophin-4 (NT-4). See Anand P: Neurotrophins and peripheral neuropathy, Philos Trans R Soc Lond B Biol Sci 1996, 351:449-454; NGF has been recognized as an important mediator of chronic pain, arising from various pathological conditions such as osteoarthritis, low back or spinal injuries, cancer, and urological chronic pelvic pain. NGF is also known to play a key role in the generation of acute and chronic pain and in hyperalgesia in diverse pain states, where NGF is expressed at high levels in damaged or inflamed tissues and facilitates pain transmission by nociceptive neurons through a variety of mechanisms. NGF has been shown to be upregulated in a subset of individuals suffering from such pain syndromes. Kumar et al. J Pain Res. 2012; 5:279-87. doi: 10.2147/JPR.S33408. Epub 2012 Aug. 17. Introduction of the CD271 specific aptamer can compete for binding sites and block NGF binding to CD271 expressing cells.

Furthermore, NGF has been found to be deficient in diabetics, leading to complications in neurons and fibers. Deficits of NGF transport, serum and tissue content have been demonstrated in experimental diabetes, which is often characterized by major complications such as dysfunction and degeneration of several types of PNS neurons/fibers. Sensory involvement is predominant, the small diameter sensory fiber degeneration being responsible for the more debilitating symptoms. On the other hand NGF supply in animal models of diabetic neuropathies reverses neuropathic signs, by protecting the affected PNS neurons and normalizing their activity. See Fischer W, Wictorin K, Bjorklund A, Williams L R, Varon S, Gage F H: Decreasing NGF is known to play a role in the pathogenesis of diabetic neuropathy, and therefore the aptamers of the invention can provide a mechanism for molecule delivery. See Hellweg et al., "Endogenous levels of nerve growth factor (NGF) are altered in experimental diabetes mellitus: a possible role for NGF in the pathogenesis of diabetic neuropathy," J Neurosci Res. 1990 June; 26(2):258-67.

In some embodiments, aptamers of the invention can be utilized for the delivery of NGF to localized regions within an organism. In other embodiments, aptamers can be utilized for the binding of NGF to reduce NGF concentrations. For example, NGF is a known promoter of vascular-endothelial growth factor (VEGF) and neo-vascularization and can be utilized in treatment of tissues for ischemia via localized targeted delivery. See Kermani et al., J Clin Invest. 2005 Mar. 1; 115(3): 653-663; Lazarovici P, Marcinkiewicz C, Lelkes P I: Cross talk between the cardiovascular and nervous systems: neurotrophic effects of vascular endothelial growth factor (VEGF) and angiogenic effects of nerve growth factor (NGF)-implications in drug development, Curr Pharm Des 2006, 12:2609-2622. Also, NGF is a therapeutic in ophthalmology evidenced by retinal cells being receptive to the action of NGF. It has been reported that NGF induces modification of pre-synaptic elements in adult visual system, prevents the shift in ocular dominance distribution of visual cortical neurons and promotes functional recovery of retinal ganglion cells (RGC) after ischemia, delays retinal degeneration in rodents with inherited retinopathy, and reduces retinal damages in rabbits with ocular hypertension. Turner J E, Delaney R K: Retinal ganglion cell response to axotomy and nerve growth factor in the regenerating visual system of the newt (Notophthalmus viridescens): an ultrastructural morphometric analysis, Brain Res 1979, 171:197-212; and Yip H K, Johnson E M Jr: Retrograde transport of nerve growth factor in lesioned goldfish retinal ganglion cells, J Neurosci 1983, 3:2172-2182. Aptamers of the invention can be utilized to deliver NGF by binding to CD271 expressing cells in an organism.

Drug Delivery

Aspects of the invention utilize the CD271 specific aptamer for the targeted delivery of a therapeutic agent for initiating a therapeutic response. Common known pathways include transdermal, transmucal, nasal, ocular and pulmonary routes. Drug delivery systems may include liposomes, proliposomes, microspheres, gels, prodrugs, cyclodextrins, etc. Aspects of the invention utilize nanoparticles composed of biodegradable polymers to be transferred into an aerosol for targeting of specific sites or cell populations in the lung, providing for the release of the drug in a predetermined manner and degradation within an acceptable period of time. Controlled-release technology (CRT), such as transdermal and transmucosal controlled-release delivery systems, nasal and buccal aerosol sprays, drug-impregnated lozenges, encapsulated cells, oral soft gels, iontophoretic devices to administer drugs through skin, and a variety of programmable, implanted drug-delivery devices are used in conjunction with the aptamers of the invention of accomplishing targeted and controlled delivery.

For example, in the therapeutic applications discussed above, aptamer-based delivery of chemotherapy drugs (e.g. doxorubicin, docetaxel, daunorubicin, and cisplatin), toxins (e.g. gelonin and various photodynamic therapy agents), and a variety of small interfering RNAs are accomplished by any of the pathways discussed above. See Zhang et al., Tumor-Targeted Drug Delivery with Aptamers, Curr Med Chem. 2011 Sep. 1; 18(27): 4185-4194.

In some embodiments, the aptamers are conjugated to nano-systems for systemic cancer therapy, such as liposomes, albumin-based particles, PEGylated proteins, biodegradable polymer-drug composites, polymeric micelles, dendrimers, among others. Davis M E, Chen Z G, Shin D M. Nanoparticle therapeutics: an emerging treatment modality for cancer. Nat Rev Drug Discov. 2008; 7:771-782.

Long circulating macromolecular carriers such as liposomes, can exploit the enhanced permeability and retention effect for preferential extravasation from tumor vessels. See Biomaterials. 1995 January; 16(2):145-8. In certain embodiments, the CD271 specific aptamers of the invention are conjugated to a liposome or polymerosome for delivery of a drug. For example, liposomal anthracyclines have achieved highly efficient drug encapsulation, resulting in significant anticancer activity with reduced cardiotoxicity, and include versions with greatly prolonged circulation such as liposomal daunorubicin and pegylated liposomal doxorubicin. See Krishna et al., Carboxymethylcellulose-sodium based transdermal drug delivery system for propranolol, J Pharm Pharmacol. 1996 April; 48(4):367-70. Pegylated liposomal doxorubicin has shown substantial efficacy in breast cancer treatment both as monotherapy and in combination with other chemotherapeutics. To accomplish true molecular targeting, the ligand-directed aptamers of the invention represent an integration of biological components capable of tumor recognition with delivery technologies Liposomal drug delivery systems provide stable formulation, provide improved pharmacokinetics, and a degree of 'passive' or 'physiological' targeting to tumor tissue. Conjugation between the CD271 specific aptamers of the invention and liposomes provides targeting of CD271 expressing cells. Encapsulation of hydrophilic and hydrophobic materials, such as potential chemotherapy agents, are known. See for example U.S. Pat. No. 5,466,468 to Schneider et al. issued Nov. 14, 1995 which discloses parenterally administrable liposome formulation comprising synthetic lipids; U.S. Pat. No. 5,580,571, issued Dec. 3, 1996 to Hostetler et al. which discloses nucleoside analogues conjugated to phospholipids; U.S. Pat. No. 5,626,869 to Nyqvist et al. issued May 6, 1997 which discloses pharmaceutical compositions wherein the pharmaceutically active compound is heparin or a fragment thereof contained in a defined lipid system comprising at least one amphiphatic and polar lipid component and at least one nonpolar lipid component.

Liposomes and polymerosomes can contain a plurality of solutions and compounds. Attachment of the CD271 specific aptamers of the invention to a liposome or polyerosome can target deliver of solutions and compounds to cells within an organism.

In certain embodiments, the aptamers of the invention are coupled to polymersomes. As a class of artificial vesicles, polymersomes are tiny hollow spheres that enclose a solution, made using amphiphilic synthetic block copolymers to form the vesicle membrane. Common polymersomes contain an aqueous solution in their core and are useful for encapsulating and protecting sensitive molecules, such as drugs, enzymes, other proteins and peptides, and DNA and RNA fragments. The polymersome membrane provides a physical barrier that isolates the encapsulated material from external materials, such as those found in biological systems. Polymerosomes can be generated from double emulsions by known techniques, see Languir 2005, 21, 9183-9186, Lorenceau et al. "Generation of Polymerosomes from Double-Emulsions."

Diagnostics

In some embodiments of the invention, the aptamers are utilized for diagnostic purposes, including histology, for the determination of treatment prognosis. For example, the aptamers of the invention can be conjugated to a detectable label and then exposed to a tumor for analysis for detection of CD271 expressing cells. For example, human melanoma is composed of distinct cell types reminiscent of neural crest derivatives and contains multipotent cells that express the neural crest stem cell markers CD271(p75NTR) and Sox10. When isolated from solid tumors by using a method that leaves intact cell surface epitopes, CD271-positive, but not CD271-negative, cells formed tumors on transplantation into nude or nonobese diabetic/severe combined immunodeficient (NOD/SCID) mice. These tumors fully mirrored the heterogeneity of the parental melanoma and could be passaged more than 5 times. Detection of CD271 positive cells can imply metastasizing tumors, providing indicators for long-term prognosis. See Civenni et al. "Human CD271-Positive Melanoma Stem Cells Associated with Metastasis Establish Tumor Heterogeneity and Long-term Growth," Cancer Res Apr. 15, 2011 71; 3098.

In some embodiments, the aptamers of the invention can be beneficial in detection of proteins as indicators of cancer onset. For example, Ewing's family tumor (EFT) is a rare pediatric tumor of unclear origin that occurs in bone and soft tissue. Specific chromosomal translocations found in EFT cause EWS to fuse to a subset of transcription factor genes (ETS), generating chimeric EWS/ETS proteins. These proteins are believed to play a crucial role in the onset and progression of EFT. EWS/ETS also induced immunophenotypic changes in mesenchymal progenitor cells, including the disappearance of the mesenchyme-positive markers CD10 and CD13 and the up-regulation of the EFT-positive markers CD54, CD99, CD117, and CD271. See Miyagawa et al. "Inducible Expression of Chimeric EWS/ETS Proteins Confers Ewing's Family Tumor-Like Phenotypes to Human Mesenchymal Progenitor Cells" Mol. Cell. Biol. April 2008 vol. 28 no. 7 2125-2137. In some embodiments, the aptamers of the invention can be a predictor of the likelihood of response to therapeutic treatments. For example, the expression of CD271 on breast cancer tumors can be a predictor of therapeutic response to breast cancer treatments in an analysis of bone marrow tissues. See Kim et al. PNAS, vol. 109 no. 16, doi: 10.1073/pnas.1203203109, where a positive correlation was found between mesenchymal stem cells expressing GD2 and CD271 and breast cancer-initiating cells in bone marrow of patients with primary breast cancer.

Attaching Aptamers to Scaffolds

Another aspect of the invention provides an implantable medical product. The product includes a scaffold composed of a biocompatible material, and a plurality of nucleic acid ligands that binds to CD271. The nucleic acid ligands may include the nucleotide sequence of SEQ ID NO: 1 or the nucleotide sequence of SEQ ID NO: 2. Once implanted, the aptamers will attach adult stem cells that express CD271, such as mesenchymal stem cells. The increased rate of adult stem cell retention results in increased density of somatic tissue cells generated on the surface of the implant, providing an increased rate of tissue regeneration.

Any scaffold known in the art may be used. The scaffold may be porous or non-porous. The nucleic acid ligands may be coupled to an external surface of the scaffold. When porous, the ligands may be coupled to either or both an internal or external surface of the scaffold. The scaffold may also be bioresorbable.

Aptamers of the invention may be coupled to an implantable medical product by known means, as discussed above by chemically modifying the CD271 specific aptamers. For example, aptamers of the invention may be coupled to the scaffold, via a binding pair, or other attachment strategies known in the art. The methods of attaching labels to the aptamer may be used to attach the aptamer to the scaffold. Other attachment strategies are also shown in Hoffmann et al. (J Biomed Mater Res A., 84(3):614-21, 2008) and Avci-Adali et al. (HP Eur Cell Mater. 21:157-176, 2011), the content of each of which is incorporated by reference herein in its entirety.

In some embodiments of the invention, the aptamers are conjugated to an implantable medical device. For example, porous medical implant devices, particularly of metallic, ceramic or polymeric construction, but also those of biological origin, have proven of great value as scaffolds for tissue growth in medical applications. Implantable medical devices can include stents, screws, or artificial joints, whereby bioactive materials such as stem cells can be immobilized and concentrated on the surfaces. The aptamers conjugated to the implantable device can selectively bind CD271 expression cells, or stem cells, to the region undergoing tissue regeneration.

Implantable medical products can also include a scaffold. Scaffolds, or three-dimensional artificial structures inserted into an organism, can promote stem cell attachment and migration, deliver and retain cells and biochemical factors, enable diffusion of vital cell nutrients and expressed products, and exert certain mechanical and biological influences to modify the behavior of the cell phase. Tissue engineering medical devices require a biomaterial scaffold as a critical component of the system, cells (often stem cells) and a bioreactor to provide an environment with appropriate signals to the cells (chemical, biochemical, mechanical and/or electrical, depending on the nature of the tissue to be grown). The scaffolds provide a temporary structure upon which cells adhere, migrate, replicate and differentiate into new tissue structures (extracellular matrix) over time. Thus, the biomaterial scaffold is at the center of any successful tissue engineering strategy and provides many essential features and cues to direct the cells toward a functional outcome.

In some aspects of the invention, the scaffold is a collagen-based matrix prepared as a honeycomb, lattice, sponge or any other similar structure made of a biocompatible and/or biodegradable collagen containing material of defined density and porosity that is pliable, storable and, most importantly, highly porous.

In some embodiments, aptamers of the invention are conjugated to a hydrogel, which is used as a scaffolding material, owing to their highly swollen network structure, ability to encapsulate cells and bioactive molecules, and efficient mass transfer. Various polymers, including natural, synthetic and natural/synthetic hybrid polymers, can be used to make hydrogels via chemical or physical crosslinking. See Zhu et al, Design properties of hydrogel tissue-engineering scaffolds, September 2011, Vol. 8, No. 5, Pages 607-626 (doi: 10.1586/erd.11.27).

In some embodiments aptamers are bound to synthetic bioactive and bioresorbable composite materials used as scaffolds for tissue engineering. See Boccaccini et al., Bioactive composite materials for tissue engineering scaffolds, May 2005, Vol. 2, No. 3, Pages 303-317 (doi:10.1586/17434440.2.3.303). Additionally, aptamers of the present invention can be bound to carbon nanotubes utilized in tissue engineering. See Edwards et al., Carbon nanotubes in scaffolds for tissue engineering, September 2009, Vol. 6, No. 5, Pages 499-505 (doi:10.1586/erd.09.29)

In some embodiments of the invention, CD271 specific aptamers are conjugated to a coronary stent inserted during coronary angioplasty to correct arterial stenosis. It should be appreciated that numerous implantable device can be conjugated to the CD271 specific aptamer of the invention as a means of promoting tissue regeneration.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

CD271 Source

As the source of CD271 molecules, a Sigma-Aldrich product [PN: N8898, NERVE GROWTH FACTOR RECEPTOR (NGF R, p75 NEUROTROPHIN R)/Fc CHIMERA Human, Recombinant, http://www.sigmaaldrich.com/etc/medialib/docs/Sigma/Datasheet/4/n8898dat.Par.0001.File.tmp/n8898dat.pdf] was used. The additional chimeric moiety of this protein is presented by human IgG1 Fc fragment. Furthermore, the CD271 chimeric protein is supplied in a form of lyophilized powder containing PBS salts and BSA. Thus, the received Sigma product contained 50 µg of the CD271 chimeric protein and 2.5 mg of BSA. The molecular weight of the CD271 bearing chimera is ~100 kDa. The BSA MW is ~67.0 kDa. However, aggregation of BSA molecules during storage/aging may lead to formation of high molecular weight BSA adducts. The native PAGE of the Sigma product was performed using Protean II mini-cell, the native sample buffer, 4-20% Ready Gels, and Tris-HCl running buffer (all from BioRad). The protein bands were developed using silver staining kit and procedures (BioRad). The gel photograph is shown in FIG. 2.

Figures 2, 3:
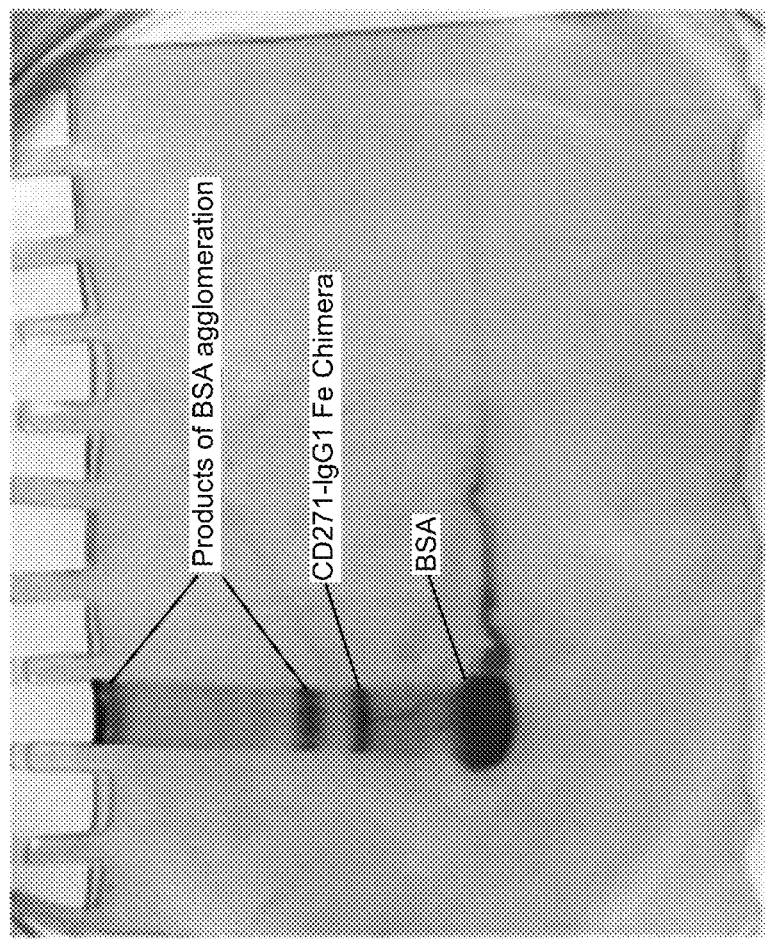
FIG. 2 is a photograph of the N8898 CD271-chimera product gel-gram. The product was reconstituted in 100 µL of HPLC grade water. 10 µL of the resultant solution was mixed with 5 µL of the native sample buffer and applied on the gel. The protein application was performed once. The electrophoresis of the same originally loaded protein was performed twice under 200 V for 45 min.
FIG. 3 is an exemplary set of sequences for the starting DNA oligonucleotide library.

From the bottom to the top of the gel, FIG. 2 shows an overloaded band of BSA, and, putatively, one band of chimeric CD271 and one band of BSA dimer. The top of the gel shows presence of material that can be assigned to the presence of highly agglomerated BSA. Importantly, during the run, the abundant band of BSA was easily observed as a blue color spot due to formation of a complex of negatively charged amino acid residues of BSA and the positively charged witness dye (Coomassie blue), which simplified locating the DNA-CD271 gel segment.

It is noteworthy to mention that based on our previous experience, the multiple runs of proteins within the same 4-20% gradient gel under conditions of high voltage results in trapping the proteins within a certain zone of the gel density gradient during the first electrophoretic run. Therefore, the next runs dID not substantially change the positions of the individual bands. This feature of the gradient gels was further applied for isolation of the DNA aptamer molecule pool specific to the CD271-IgG1 FC chimera.

Example 2

Candidate Mixture

The mixture of the custom made DNA oligonucleotides was specifically made for us and at our direction by Sigma-Aldrich. The mixture of the custom made DNA oligonucleotides was presented by the 70-mer DNA sequences containing flanking primer regions and a middle 28-nt randomly varied segment. This DNA general structure is shown below (FIG. 3).

Example 3

Aptamer Identification

In order to identify the DNA sequences capable of retention by CD271, the following was performed:

One-time gel separation of the remaining solution of CD271 in 7 separate gel lanes as described above.

Electrophoresis of the 15 μL of 100 mM solution of the Randomer plus 5 μL sample buffer in each well of the same gel under the same conditions (total 220 μg DNA)

The gel segment between the BSA monomer and dimer band was cut and collected in a 50-mL sterile Falcon tube. The gel segment was washed 7×30 mL of Nuclease Free water (NF-water) with vigorous vortexing to remove unbound DNA.

The washed gel was immersed in 2.00 mL of the saturated solution of sodium thiocyanate (NaSCN, chaotropic agent) and vortexerd for 30 min to release the bound DNA.

The released DNA was purified from NaSCN using the QIAquick Nucleotide Removal Kit (Qiagen), concentrated to 70 μL by lyophilization and used to repeat the above described aptamer isolation steps once more.

The resultant DNA aptamer pool (490 μL) was used to perform the negative selection process.

Example 4

Negative Selection

The process of negative selection was performed to remove from the DNA aptamer pool sequences corresponding to:

PAGE used for protein trapping.

IgG1 (IgG1 Fc is a portion of the Sigma CD271 product).

BSA (possible slight overlap with the CD271 chimera).

To select against BSA and IgG1, these proteins (BSA fraction V and human IgG1, kappa, both from Sigma-Aldrich) were immobilized on approximately 100 mg of Zirconia/Silica beads each (BioSpec Products, Inc.) using the following scheme (Scheme 1).

Scheme 1. Protein binding via aldehyde activation of the beads.

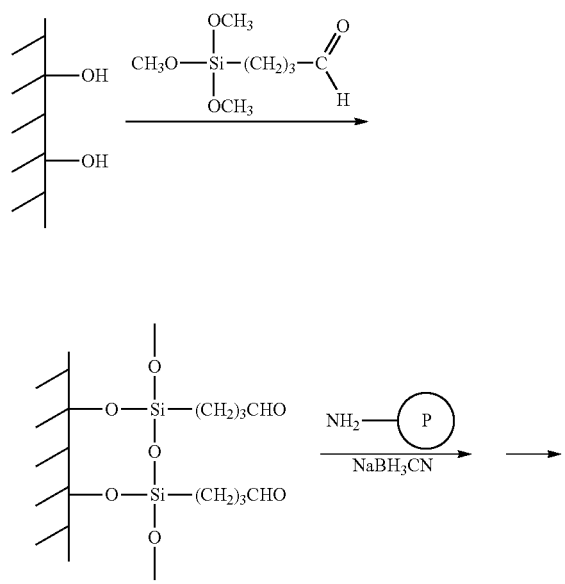

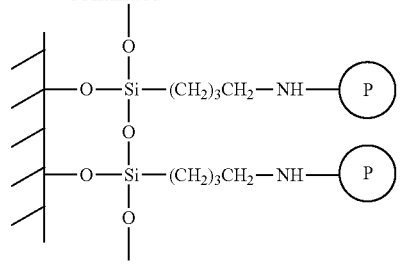

This procedure included the following steps:

A. Bead Activation:

Immersing the beads in 1 mL of 1% ethanol solution of 3-(trimethoxysilyl)butyl aldehyde [United Chemical Technologies, Bristol, Pa. PNo; PSX1050]

Incubation for 30 min at room temperature

Washing with 5 volumes of with absolute ethanol

Removal of ethanol by decantation and heating the beads at 120° C. for 15 min.

The above procedure results in the formation of a thin coating of butyl aldehyde functionalities ready for protein attachment.

B: Bead Decoration:

The activated beads were immersed in 1.0 mL 50 mM PBS, pH 8.0, and containing 1 mg of the targeted proteins supplied with sodium cyanoborohydride to the 4 mM concentration. Under these conditions 10.5% of IgG1 and 8.0% of BSA was bound to the beads after an overnight exposure. The beads were thoroughly washed with copious amounts of fresh buffer; so that no protein was detected spectrophotometrically at 280 nm. As long as relatively high protein to bead mass ratio (10:1) was used, no further blocking of beads was performed.

The overall process resulted in beads prepared for adsorption of DNA sequences specific to IgG1 and BSA possibly present in the aptamer pool.

The negative selection was performed by mixing the aptamer pool, a segment of neat polyacrylamide gel and the decorated beads for one hour at room temperature in a 15-mL Falcon tube on a rotary shaker.

At the end, the supernatant was collected by centrifugation and used for PCR amplification of the DNA aptamers specific to CD271.

Example 5

PCR Amplification

Figure 4:
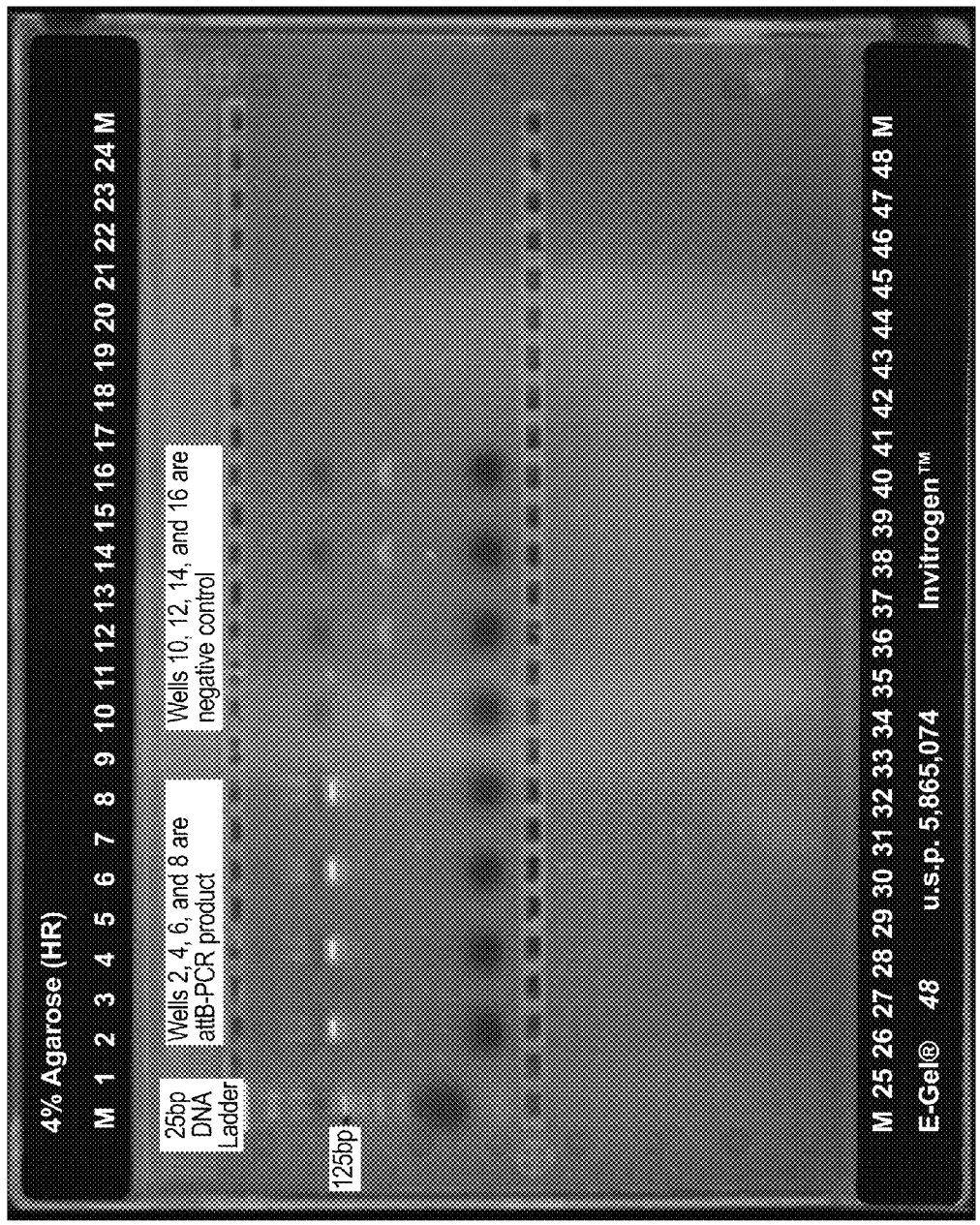
FIG. 4 is a photograph of an agarose gel of the aptamer pool PCR product.

The aptamer amplification was performed as follows. Initial denaturation at 95° C. for 2 min and 30 cycles (repeats) of denaturation at 95° C. for 15 s, primer annealing at 50° C. for 30 s and elongation at 68° C. for 30 s. The amplified aptamer solution was evaluated by gel electrophoresis (FIG. 4).

The gel showed presence of amplicons in the test wells and no potential impurities or non-specific amplification within the control wells. Thus, the amplified product was judged to be ready for molecular cloning and sequencing to be performed during the next interim.

Figure 5:
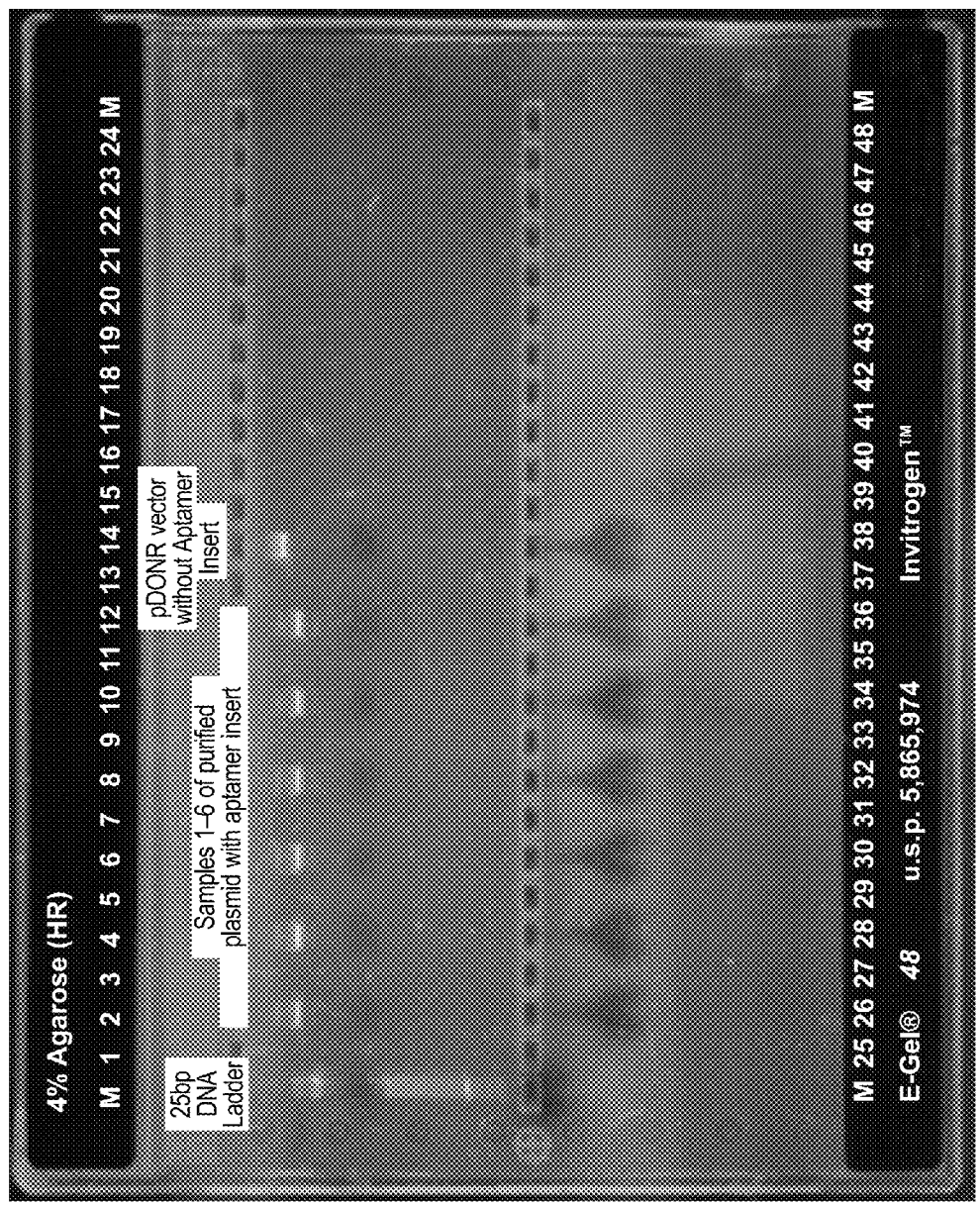
FIG. 5 is a photograph of aptamer containing (smaller size) vs intact plasmid (larger size) migration in the agarose gel.

The cloning process was performed using the PCR amplified aptamers and aptamer-plasmid insertion and resistance marker selection kit, and according to the procedures obtained from Invitrogen (PCR CLONING SYSTEM WITH GATEWAY (PCR kit) Technology with pDONR/Zeo and OmniMAX2 Competent Cells; PN #12535-037). The cloning process involves replacement of a gene insert in the vector plasmid by the aptamers sequence. As long as the size of the replaced insert is significantly larger than the size of the used DNA oligonucleotide, a shift in the plasmid size is expected upon a successful cloning event. The successful resultant cloning was monitored through the competent cell resistance marker (ZEOCIN) and was confirmed by reduction of the plasmid size as shown in FIG. 5.

The aptamer sequences were obtained via analysis of the DNA fragment inserts recovered from the competent cells at IST. The cloned material was sequenced at the Dana Farber Cancer Institute. The software package Chromas Lite version 2.01 was used to extract aptamer region from sequencing chromatogram data files. Out of 48 samples, only 42 samples were able to sequence. Only aptamer with 70-base sequences were used for analysis. The sequences are provided below in FIGS. 6A-B.

The folding patterns and thermodynamic properties (ΔG and Tm) of these sequences were obtained using the on-line software package at Integrated DNA Technologies. The candidates showing higher frequency of the structural repeatability and within a medium thermodynamic property range within the isolated aptamer pool were further selected for synthesis and evaluation at IST. Additionally, the aptamer pool was analyzed for the most probable sequence motif best fitting the aptamer pool. FIGS. 6A-B shows the alignment of only 70 bases sequenced aptamers including the consensus using ClustalW2 software.

Figure 7B:
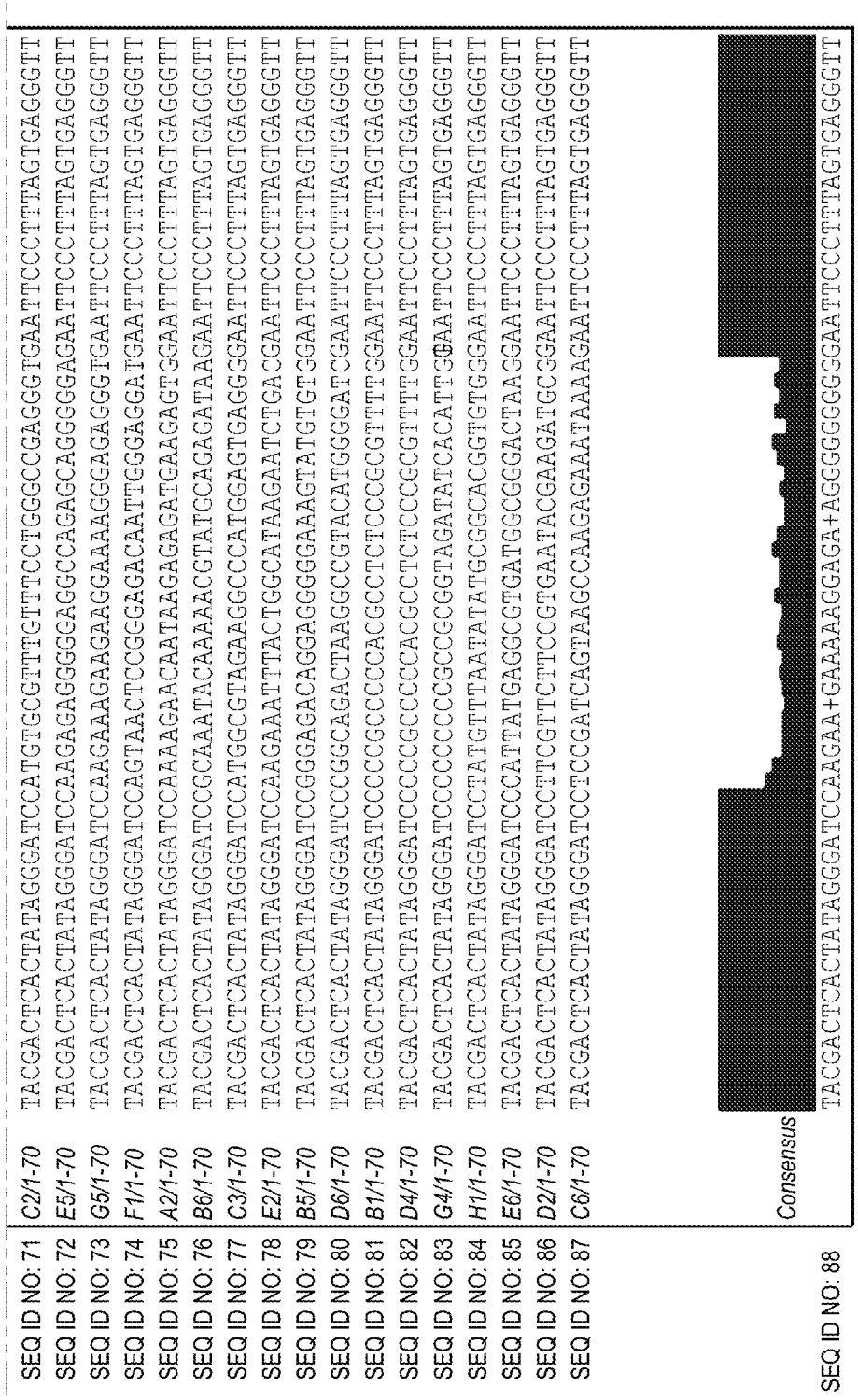

Furthermore, the sequenced aptamers were compared for their structural similarity using direct calculations of the matching oligonucleotides using ClustalW2 software; thus the average aptamer pool motif was determined (FIGS. 7A-B).

Figure 9:
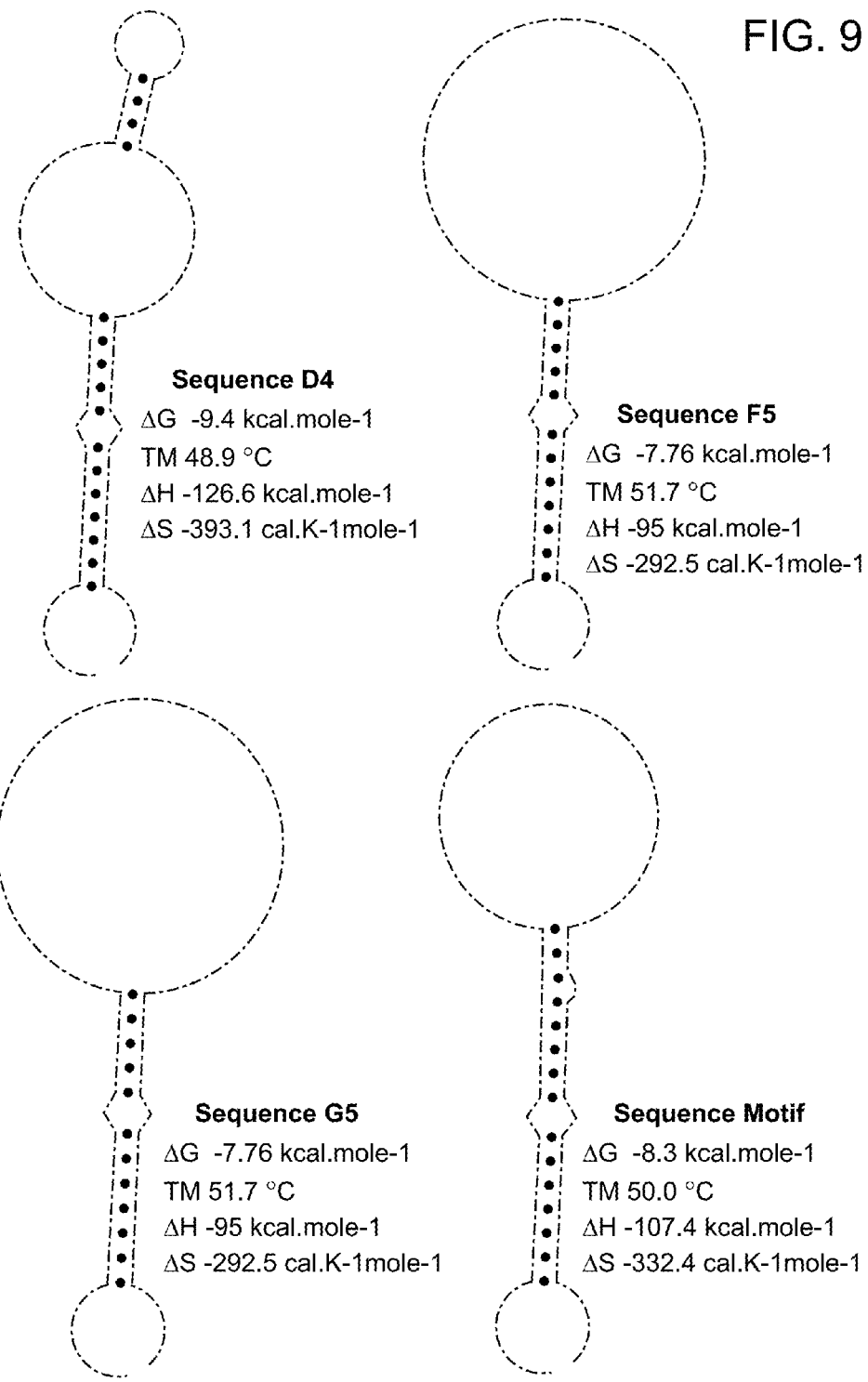
FIG. 9 shows the aptamer folded structures.

FIGS. 8A-B shows the similarity scores of the sequenced aptamer pool along with the motif. It is noteworthy to mention that based on the data shown in the score column in FIGS. 8A-B, there were two pairs of sequence; B1&D4 and C5& F5 that are exactly identical. Also, the sequence G5 was 90% similar to the determined motif. Sequences D4, G5, F5, and motif were synthesized at Integrated DNA Technologies in some mg quantities for evaluation of the aptamer binding affinities to CD271. The folded structures of these aptamers are presented in FIG. 9.

Binding of the motif aptamer to the target protein was confirmed using size exclusion HPLC. To this end, mixtures containing different molar ratios of protein to aptamer were prepared and incubated at room temperature. As the source of aptamer, the average motif structure determined in the previous monthly report was used. The 0.1-mL aliquots of the mixtures were injected on the Shodex size exclusion column and eluted using 0.01 M PBS pH7.4 solution. The instrument description and the elution conditions are provided below:

Waters high pressure liquid gradient chromatography (HPLC), including Empower 2 software package, 2695 Separation Module, Autosampler/injector, 2996 Photodiode Array Detector, Automatic Fraction Collector, and Superdex 200 10/300 GL column (GE Healthcare Europe GmbH, Uppsala, Sweden).

Flow rate, 0.4 mL/min, room temperatures (uncontrolled), detection at 254 nm.

Figure 10:
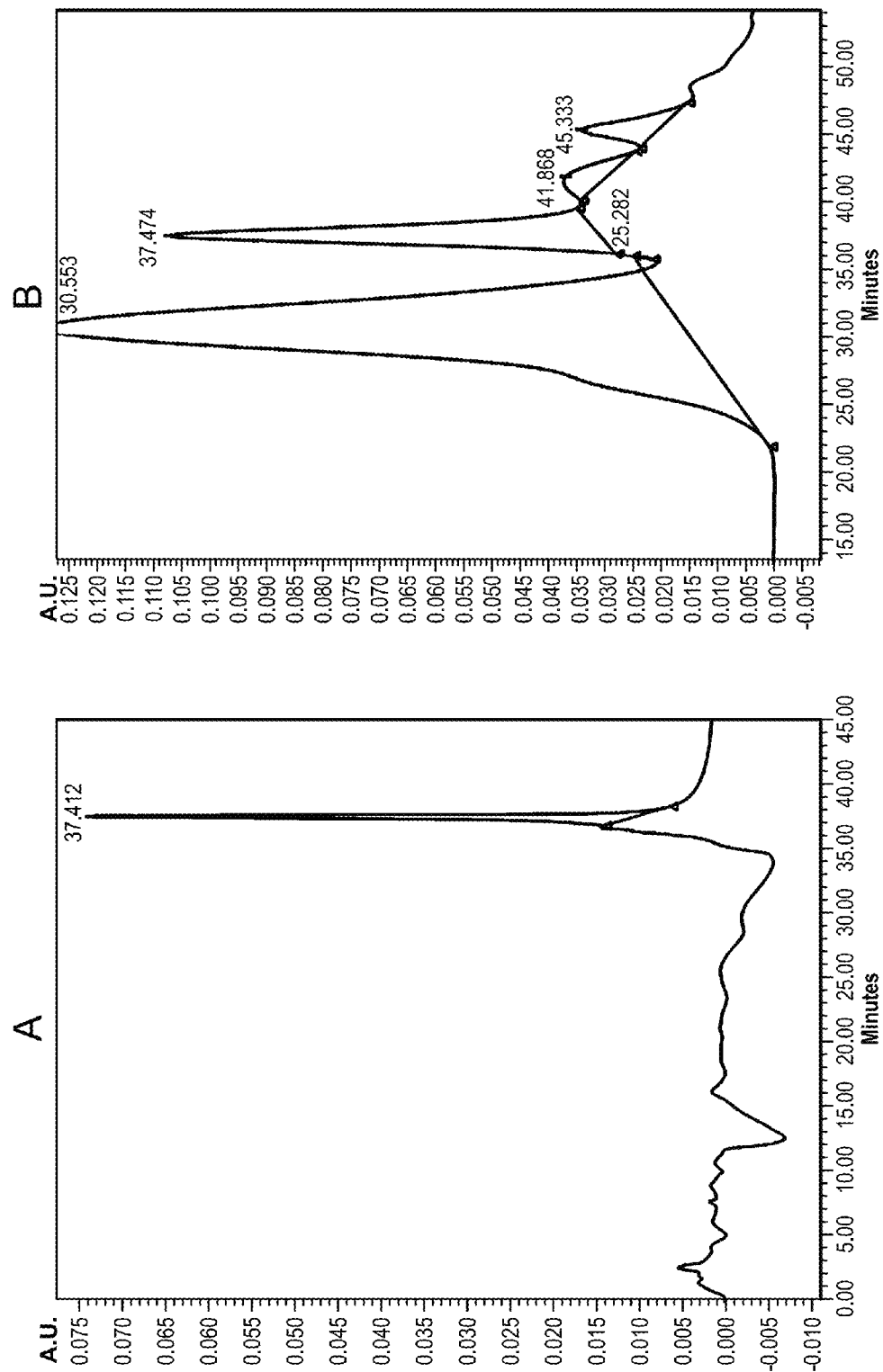
FIG. 10 panels A-B show chromatograms of neat target protein (A) and neat motif aptamer (B).

Chromatograms of neat aptamer and target protein were also recorded. The HPLC results are provided below. FIG. 10 panels A-B shows chromatograms of the reagents (aptamer and protein). It can be seen that the reagents contained differently aggregated species, as several peaks for each of the reagents were observed at different retention times. However, it should be noted that none of the reagents had detectable material at the retention times lower than 30.0 min.

Figure 11:
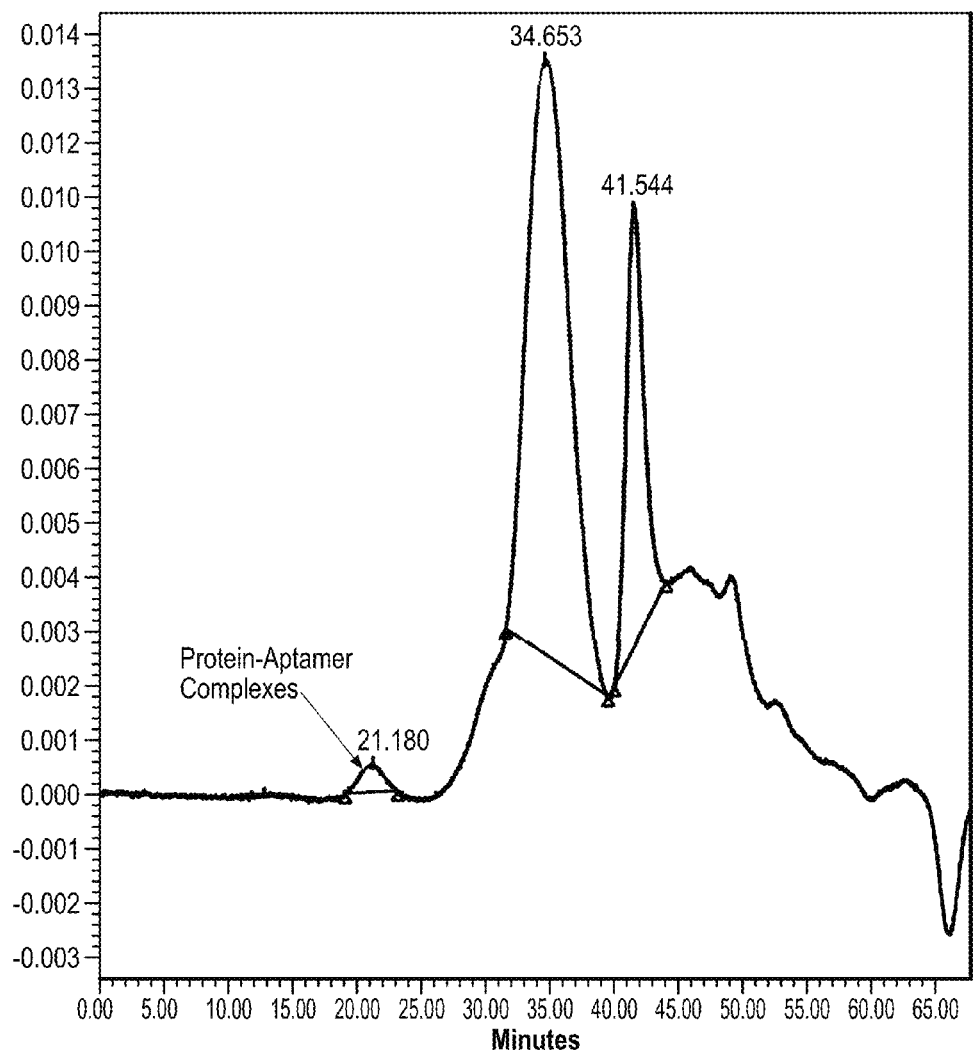
FIG. 11 shows a chromatogram of the aptamer-protein mixture (aptamer to protein 5:1 molar ratio).

On the other hand, FIG. 11 shows presence of high molecular weight aggregates eluted at 21.2 min. As long as higher molecular weight compounds are eluted earlier during size exclusion HPLC, and there is a substantial reduction of the elution time (more than 10 min if compared with the aptamer aggregates and almost 20 min if compared with the neat protein) this findings confirm formation of the a complex by reaction of aptamer and protein molecules.

The motif sequence of the CD-271 specific aptamer generated in the tris-HCl PAGE buffer was designated as 1391-Motif. The sequence for the 1391-Motif is as follows:

(SEQ ID NO: 1)
TACGACTCACTATAGGGATCCAAGAAAGAAAAAGGAGAAAGGGGGGGGG

AATTCCCTTTAGTGAGGGTT

The affinity of 1391-motif structure was further evaluated by Surface Plasmon Resonance (SPR) at SensiQ Technologies (Oklahoma City, Okla.) as described in Section 1.6.1 "Determination of the aptamer affinity by SPR".

Example 6

Isolation of Aptamer Using Dulbecco's Phosphate-Buffered Saline (DPBS)

The overall isolation process was performed as described above (Aptamer isolated in Tris-HCl buffer); however, the electrophoretic run of the DNA library over CD271 trapped in the gel was performed in DPBS pH 7.4 to mimic the physiological conditions.

Furthermore, four individual aptamer candidates were evaluated in a chromogenic ELISA assay to compare their affinity to CD271. Based on the rate of signal increase in an ELISA assay, one aptamer designated as 1470-G1 was selected for future determination of its affinity to CD271. The sequence for the 1470-G1 is as follows:

(SEQ ID NO: 2)
TACGACTCACTATAGGGATCCCACCCCGCGGGCCCCCCCACAGCCTCGCG

AATTCCCTTTAGTGAGGGTT

Example 7

Determination of the Aptamer Affinity by SPR

The SPR affinity detection was performed according to the standard SPR assay protocols established at SensiQ and using PBS pH 7.4. The biotinylated forms of 1391-motif and 1470-G1 aptamers were immobilized on the SPR chips in this assay. In parallel, randomly scrambled aptamer sequences were used to rule out non-specific binding of CD271 by DNA oligonucleotides.

Figure 12:
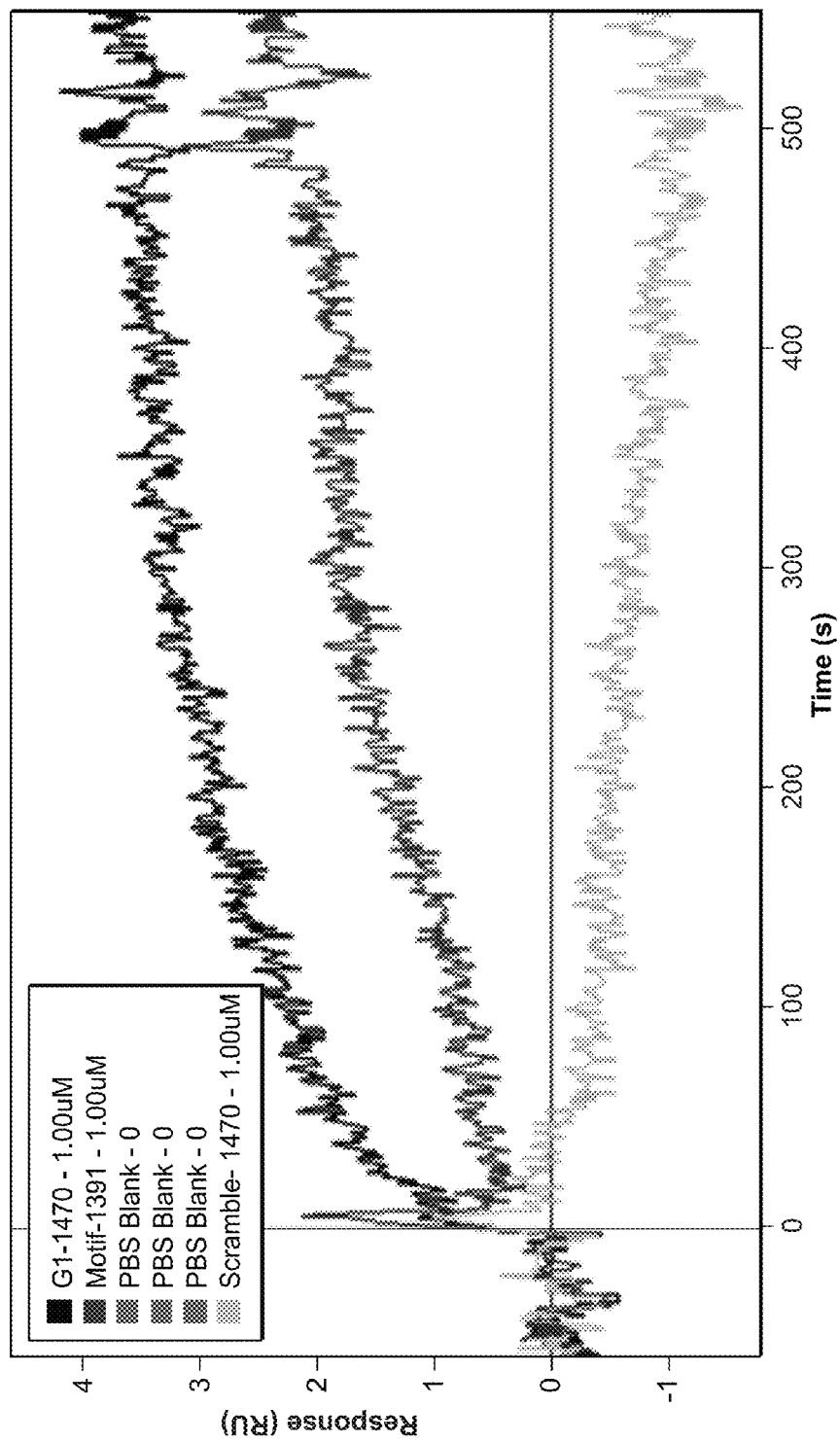
FIG. 12 shows absorbance of CD271 as function of the capturing DNA oligonucleotide on the SPR test chips. 1470-G1 (black curve); 1391-Motif (blue curve); 1470-Scramble (green curve).

The constants of dissociation (Kd) of the aptamer-CD271 complexes were used to assess the aptamer affinity. It was determined that the Kd for the 1391-motif and 1470-G1 aptamers were 1.1 and 19.5 nM respectively. No binding of CD271 to scrambled aptamers was observed. FIG. 12 illustrates the results of the SPR assay. Table 1 below summarizes properties of the selected aptamers.

TABLE 1

Properties of the CD271 specific aptamers

| Designation | ssDNA sequence | Kd (nM) |
|---|---|---|
| 1470-G1 | TACGACTCACTATAGGGATCCCACCCCGC GGGCCCCCCCACAGCCTCGCGAATTCCCT TTAGTGAGGGTT (SEQ ID NO: 2) | 1.1 |
| 1391-Motif | TACGACTCACTATAGGGATCCAAGAAAGA AAAAGGAGAAAGGGGGGGGGAATTCCC TTTAGTGAGGGTT (SEQ ID NO: 1) | 19.5 |

These aptamers show high affinity to CD271.

Example 8

Effect of the CD271 Aptamer on Cells Sensitive to NGF

Figure 13:
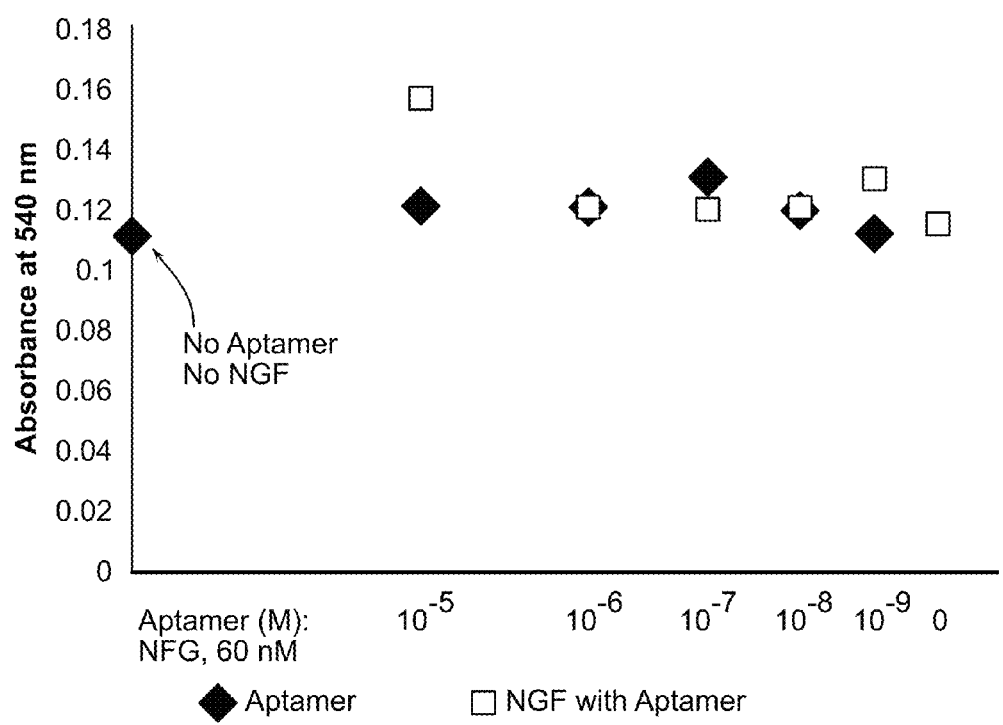
FIG. 13 is a graph showing the effect of aptamer concentration on SK-N-MC counts as a function of the aptamer concentration.

NGF, a neurotrophin, binds to transmembrane proteins CD271 as well as trkA to mediate different cellular processes and signals in cells, including neurite outgrowth, pain, cell survival, and apoptosis. Based on evidence in literature, cells containing both receptors, CD271 and trkA, can exhibit growth when exposed to NGF. However, cells containing only CD271 may initiate apoptosis when exposed to NGF (Niederhauser et al, 2000). The SK-N-MC cells, human neuroepithelioma cells, only contain CD271 (Niederhauser et al 2000). FIG. 13 shows that aptamers of the invention can inhibit binding of NGF to CD271, and that in this case the cells would survive better when treated with the aptamer and NGF.

Cell Culture

SK-N-MC cells were grown in complete growth medium containing 89% Eagle's Minimum Essential Medium (EMEM), 10% deactivated fetal bovine serum, and 1% penicillin-streptomycin at 37° C. and 5% CO2 in a humidified environment. The serum was deactivated at 56.0° C. The temperature was monitored with an aliquot of serum that was run in parallel to the sterile aliquot. Once the temperature reached 56.0° C. in the aliquot, the serum was allowed to sit in the water bath for 30 min with gentle shaking every ten minutes. In order to subculture the cells, the medium was removed and the cells were briefly rinsed with approximately 1 ml of trypsin solution. After the trypsin solution was discarded, 2-3 ml of trypsin was added to the cells again, and the cells were allowed to incubate for 10-15 min at 37° C. and 5% $CO_2$ in order to facilitate detachment. Approximately 30 ml of complete growth medium was added to the cells that were detached. The following solution was then split between 3-4 culture flasks that were allowed to incubate until the following passage.

Cell Treatment

Cells were allowed to grow until at least the third passage for the experiment. Confluent cells were detached from the culture flask using trypsin as described above and were replenished with about 10 ml of complete growth medium. The cells were aspirated to ensure an even cell suspension. A small sample was removed in order to determine the cell concentration using a hemocytometer. 20 µl of the suspension was used in each chamber of the hemocytometer slide. The 5×5 center grid of the hemocytometer had a volume of 0.1 µl. The cells were diluted to a final concentration of $10^6$ cells/ml. 100 µl of cells or medium alone were added to the wells of a 96-well tissue culture treated plate according to the attached protocol. The plate was allowed to incubate at 37° C., 5% $CO_2$ for varying amounts of time, even though the literature states three days.

NGF was reconstituted in complete growth medium to a final concentration of $7.2 \times 10^{-13}$ mol/µl. Aptamer was reconstituted in complete growth medium to a final concentration of $1.2 \times 10^{-9}$ mol/µl. NGF was always added to a final concentration of 60 nM, and aptamer was added to a final concentration of either $10^{-9}$ M, $10^{-8}$ M, $10^{-7}$ M, $10^{-6}$ M, or $10^{-5}$ M in the controls and in equivalent concentrations in the experimental groups with 60 nM NGF. 20 µl of complete growth medium, NGF, aptamer, or NGF and aptamer solution were added to the cells in the plate. The cells were allowed to incubate for 24 hours at 37° C., 5% $CO_2$.

Cell Viability and NGF Analysis

Whether or not the cells were adherent was determined by removing the supernatant of a non-experimental well and treating the remaining cells with trypsin. The cell count and cell viability using trypan blue was obtained from both solutions. If the cells were adherent, the supernatant was removed for NGF analysis, and the cells were replenished with an equal volume of fresh medium for the MTT assay. If the cells were not adherent, the MTT assay was performed directly in the wells of the plate. The reconstituted MTT solution was added to the wells at 10% of the initial volume in each well. The plate was allowed to incubate for 2-4 hrs at 37° C., 5% $CO_2$ for 2-4 hours, or until purple crystals formed. MTT solubilization solution was added to each well so that the crystals were completely dissolved. The absorbance was measured at 540 nm with a reference wavelength of 650 nm.

NGF concentrations in the wells were also determined by using the NGF ELISA kit and protocol provided by Abcam. See Niederhauser O, Mangold M, Schubenel R, Kusznir E A, Schmidt D, Hertel C. NGF ligand alters NGF signaling via p75(NTR) and trkA. J Neurosci Res. 2000 Aug. 1; 61(3):263-72; and Zhang Y H, Nicol G D. NGF-mediated sensitization of the excitability of rat sensory neurons is prevented by a blocking antibody to the p75 neurotrophin receptor. Neurosci Lett. 2004 Aug. 12; 366(2):187-92.

Results

As shown in FIG. 13, readings were taken at 540 nm with a reference wavelength of 650 nm. A higher absorbance value indicated higher mitochondrial activity within the cells, also indicating a higher concentration of cells. The black diamonds show the group containing only growth medium and aptamer from high to low concentration from left to right. The red squares show the group treated with NGF and aptamer from high to low concentration, and NGF alone from left to right. It was apparent that the concentration of NGF alone selected from the literature (60 nM, Niederhauser at al 2000) did not lead to the cell apoptosis. However, the highest used in the experiment concentration of aptamer (10 nM) did result in increased the cell counts.

This data shows the predicted effect of a CD271 aptamer as a ligand capable of interfering with the effect of NGF on neuronal cells. By interfering with NGF binding to CD271 as its receptor, the CD271 aptamers of the invention are useful for treating disorders caused by increased NGF concentrations such as some pain disorders. See, Zhang Y H, Nicol G D. NGF-mediated sensitization of the excitability of rat sensory neurons is prevented by a blocking antibody to the p75 neurotrophin receptor. Neurosci Lett. 2004 Aug. 12; 366(2):187-92.

What is claimed is:

1. An implantable medical product, the product comprising:
   a scaffold composed of a biocompatible material; and
   a plurality of nucleic acid ligands that binds to CD271, wherein the nucleic acid ligands comprise the nucleotide sequence of SEQ ID NO: 1 or the nucleotide sequence of SEQ ID NO: 2.

2. The product according to claim 1, wherein the scaffold is porous.

3. The product according to claim 2, wherein the ligands are coupled to an external surface of the scaffold.

4. The product according to claim 2, wherein the ligands are coupled to an internal surface of the scaffold.

5. The product according to claim 2, wherein the ligands are coupled to both an external surface and an internal surface of the scaffold.

6. The product according to claim 1, wherein the scaffold is bioresorbable.

* * * * *

SEQUENCE LISTING

<160> NUMBER OF SEQ ID NOS: 88

<210> SEQ ID NO 1
<211> LENGTH: 70
<212> TYPE: DNA
<213> ORGANISM: Artificial Sequence
<220> FEATURE:
<223> OTHER INFORMATION: Synthetic sequence

<400> SEQUENCE: 1
tacgactcac tatagggatc caagaaagaa aaaggagaaa ggggggggggg aattcccttt    60 agtgagggtt                                                            70

<210> SEQ ID NO 2
<211> LENGTH: 70
<212> TYPE: DNA
<213> ORGANISM: Artificial Sequence
<220> FEATURE:
<223> OTHER INFORMATION: Synthetic sequence

<400> SEQUENCE: 2
tacgactcac tatagggatc ccaccccgcg ggccccccca cagcctcgcg aattcccttt    60
agtgagggtt                                                            70

<210> SEQ ID NO 3
<211> LENGTH: 70
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (22)..(49)
<223> OTHER INFORMATION: n is a, t, c, or g

<400> SEQUENCE: 3
tacgactcac tatagggatc cnnnnnnnnn nnnnnnnnnn nnnnnnnnng aattcccttt    60
agtgagggtt                                                            70

<210> SEQ ID NO 4
<211> LENGTH: 21
<212> TYPE: DNA
<213> ORGANISM: Artificial Sequence
<220> FEATURE:
<223> OTHER INFORMATION: Synthetic sequence

<400> SEQUENCE: 4
tacgactcac tatagggatc c                                               21

<210> SEQ ID NO 5
<211> LENGTH: 20
<212> TYPE: DNA
<213> ORGANISM: Artificial Sequence
<220> FEATURE:
<223> OTHER INFORMATION: Synthetic sequence

<400> SEQUENCE: 5
aaccctcact aaagggaatt                                                 20

<210> SEQ ID NO 6
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 6
tacgactcac tagggatc ccccgccccc acgcctctcc cgcgttttgg aattcccttt    60
agtgagggtt    70

<210> SEQ ID NO 7
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 7
tacgactcac tagggatc cggtggggta aggtccgagg ggcgtgttgg aattcccttt    60
agtgagggtt    70

<210> SEQ ID NO 8
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 8
tacgactcac tagggatc cacgaaaggt aaactaggaa aagcagacgg aattcccttt    60
agtgagggtt    70

<210> SEQ ID NO 9
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 9
tacgactcac tagggatc caaaaaaaag caaaagacca caagagtgtg aattcccttt    60
agtgagggtt    70

<210> SEQ ID NO 10
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 10
tacgactcac tagggatc cagtaactcc gggagacaat tgggaggatg aattcccttt    60
agtgagggtt    70

<210> SEQ ID NO 11
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 11
tacgactcac tagggatc ctgcagtggg gccagttttt tatccgtgcg aattcccttt    60
agtgagggtt    70

<210> SEQ ID NO 12

```
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 12
tacgactcac tatagggatc ctatgtttaa tatatgcggc acggtgtggg aattcccttt      60
agtgagggtt                                                            70

<210> SEQ ID NO 13
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 13
tacgactcac tatagggatc caaaagaaca ataagagaga tgaagagtgg aattcccttt      60
agtgagggtt                                                            70

<210> SEQ ID NO 14
<211> LENGTH: 72
<212> TYPE: DNA
<213> ORGANISM: Artificial Sequence
<220> FEATURE:
<223> OTHER INFORMATION: SYNTHETIC SEQUENCE

<400> SEQUENCE: 14
tacgactcac tatagggatc cttaataagt ggtgacggag agagatagcg agaattccct      60
ttagtgaggg tt                                                         72

<210> SEQ ID NO 15
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 15
tacgactcac tatagggatc catgtgcgtt tgtgtcgtgg ggggagggtg aattcccttt      60
agtgagggtt                                                            70

<210> SEQ ID NO 16
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 16
tacgactcac tatagggatc cttcgttctt ccgtgaatac gaagatgcgg aattcccttt      60
agtgagggtt                                                            70

<210> SEQ ID NO 17
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 17
tacgactcac tatagggatc caagaaattt actggcataa gaatctgacg aattcccttt      60
```
agtgagggtt 70

<210> SEQ ID NO 18
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 18
tacgactcac tatagggatc ctagcgagaa gcaaaccggg gagcaaaccg aattcccttt 60
agtgagggtt 70

<210> SEQ ID NO 19
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 19
tacgactcac tatagggatc caatgggggca ttggttgaga tgttcgggag aattcccttt 60
agtgagggtt 70

<210> SEQ ID NO 20
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 20
tacgactcac tatagggatc caaagcgaaa aaaaaaaaag gcggtaattg aattcccttt 60
agtgagggtt 70

<210> SEQ ID NO 21
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 21
tacgactcac tatagggatc catggcgtag aaggccgatg gagtgagggg aattcccttt 60
agtgagggtt 70

<210> SEQ ID NO 22
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 22
tacgactcac tatagggatc cgagtgagtt gcttgattcg cccgtaagtg aattcccttt 60
agtgagggtt 70

<210> SEQ ID NO 23
<211> LENGTH: 70
<212> TYPE: DNA
<213> ORGANISM: Artificial Sequence
<220> FEATURE:

<223> OTHER INFORMATION: SYNTHETIC SEQUENCE

<400> SEQUENCE: 23

```
tacgactcac tatagggatc caaaaagaaa aagcagattc aaaaatttag aattcccttt    60
agtgagggtt                                                          70
```

<210> SEQ ID NO 24
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 24

```
tacgactcac tatagggatc cagactagac caccaagagc ctacccacag aattcccttt    60
agtgagggtt                                                          70
```

<210> SEQ ID NO 25
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 25

```
tacgactcac tatagggatc caaacagtca tgtaaggggt gagcacgaag aattcccttt    60
agtgagggtt                                                          70
```

<210> SEQ ID NO 26
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 26

```
tacgactcac tatagggatc cagcaagtgc gcaggatgaa acgtgtaggg aattcccttt    60
agtgagggtt                                                          70
```

<210> SEQ ID NO 27
<211> LENGTH: 68
<212> TYPE: DNA
<213> ORGANISM: Artificial Sequence
<220> FEATURE:
<223> OTHER INFORMATION: SYNTHETIC SEQUENCE

<400> SEQUENCE: 27

```
tacgactcac tatagggatc cggtgggggg ggaaattagg gcaggggaa ttccctttag    60
tgagggtt                                                            68
```

<210> SEQ ID NO 28
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 28

```
tacgactcac tatagggatc cggtcttgcg gtagggggtg gcggcgggtg aattcccttt    60
agtgagggtt                                                          70
```

```
<210> SEQ ID NO 29
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 29
tacgactcac tatagggatc ccccgccccc acgcctctcc cgcgttttgg aattcccttt      60
agtgagggtt                                                             70

<210> SEQ ID NO 30
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 30
tacgactcac tatagggatc caaaaaaagc ccaagataca atcatgcgag aattcccttt      60
agtgagggtt                                                             70

<210> SEQ ID NO 31
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 31
tacgactcac tatagggatc cggtgggctg gtcggggtaa ttgatcggag aattcccttt      60
agtgagggtt                                                             70

<210> SEQ ID NO 32
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 32
tacgactcac tatagggatc ccccccccgc cgcggtagat atcacattgg aattcccttt      60
agtgagggtt                                                             70

<210> SEQ ID NO 33
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 33
tacgactcac tatagggatc cagttggagc agcttctggt cagtgaatcg aattcccttt      60
agtgagggtt                                                             70

<210> SEQ ID NO 34
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 34
```

```
tacgactcac tatagggatc cgagtggggc tgcggagggt ggtggggagg aattcccttt    60
agtgagggtt                                                          70

<210> SEQ ID NO 35
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 35
tacgactcac tatagggatc cgggagacag gagggggaaa gtatgtgtgg aattcccttt    60
agtgagggtt                                                          70

<210> SEQ ID NO 36
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 36
tacgactcac tatagggatc caagcttcaa aacaaagaca actaggtgag aattcccttt    60
agtgagggtt                                                          70

<210> SEQ ID NO 37
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 37
tacgactcac tatagggatc caccatgaaa agcaaaagtt agtcaggttg aattcccttt    60
agtgagggtt                                                          70

<210> SEQ ID NO 38
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 38
tacgactcac tatagggatc caagagaggg ggaggccaga gcaggggag aattcccttt     60 agtgagggtt                                                          70

<210> SEQ ID NO 39
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 39
tacgactcac tatagggatc caagcttcaa aacaaagaca actaggtgag aattcccttt    60
agtgagggtt                                                          70

<210> SEQ ID NO 40
<211> LENGTH: 70
<212> TYPE: DNA
<213> ORGANISM: Artificial Sequence
```

```
<220> FEATURE:
<223> OTHER INFORMATION: SYNTHETIC SEQUENCE

<400> SEQUENCE: 40
tacgactcac tagggatc caagaaagaa gaaggaaaag ggagagggtg aattcccttt    60
agtgagggtt                                                        70

<210> SEQ ID NO 41
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 41
tacgactcac tagggatc caaagaaaaa aaagataaac tatggaagag aattcccttt    60
agtgagggtt                                                        70

<210> SEQ ID NO 42
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 42
tacgactcac tagggatc cgcaaataca aaaacgtatg cagagataag aattcccttt    60
agtgagggtt                                                        70

<210> SEQ ID NO 43
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 43
tacgactcac tagggatc ctccgatcag taagccaaga gaaataaagg aattcccttt    60
agtgagggtt                                                        70

<210> SEQ ID NO 44
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 44
tacgactcac tagggatc ccggcagact aaggccgtac atgggatcg aattcccttt     60 agtgagggtt                                                        70

<210> SEQ ID NO 45
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 45
tacgactcac tagggatc ccattatgag gcgtgatggc ggggctaagg aattcccttt    60
agtgagggtt                                                        70
```

<210> SEQ ID NO 46
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 46
tacgactcac tagggatc cggtgggggg ggggtgggtt ttggcttggg aattcccttt    60
agtgagggtt                                                        70

<210> SEQ ID NO 47
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 47
tacgactcac tagggatc cttgtttgtt tcacctggtg cgcatatttg aattcccttt    60
agtgagggtt                                                        70

<210> SEQ ID NO 48
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 48
tacgactcac tagggatc ctagcgagaa gcaaaccggg gagcaaaccg aattcccttt    60
agtgagggtt                                                        70

<210> SEQ ID NO 49
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 49
tacgactcac tagggatc caaacagtca tgtaaggggt gagcacgaag aattcccttt    60
agtgagggtt                                                        70

<210> SEQ ID NO 50
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 50
tacgactcac tagggatc cagttggagc agcttctggt cagtgaatcg aattcccttt    60
agtgagggtt                                                        70

<210> SEQ ID NO 51
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 51

```
tacgactcac tagggatc cgagtggggc tgcggagggt ggtggggagg aattcccttt    60
agtgagggtt                                                         70
```

<210> SEQ ID NO 52
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 52

```
tacgactcac tagggatc cacgaaaggt aaactaggaa aagcagacgg aattcccttt    60
agtgagggtt                                                         70
```

<210> SEQ ID NO 53
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 53

```
tacgactcac tagggatc cttaataagt ggtgacggag agatagcgag aattcccttt    60
agtgagggtt                                                         70
```

<210> SEQ ID NO 54
<211> LENGTH: 69
<212> TYPE: DNA
<213> ORGANISM: Artificial Sequence
<220> FEATURE:
<223> OTHER INFORMATION: SYNTHETIC SEQUENCE

<400> SEQUENCE: 54

```
tacgactcac tagggatc cagcaagtgc gcaggatgaa acgtgaggga attccctta    60 gtgagggtt                                                         69
```

<210> SEQ ID NO 55
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 55

```
tacgactcac tagggatc caaaaaaagc ccaagataca atcatgcgag aattcccttt    60
agtgagggtt                                                         70
```

<210> SEQ ID NO 56
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 56

```
tacgactcac tagggatc caaaaaaaag caaaagacca caagagtgtg aattcccttt    60
agtgagggtt                                                         70
```

<210> SEQ ID NO 57
<211> LENGTH: 70
<212> TYPE: DNA

```
<213> ORGANISM: Artificial Sequence
<220> FEATURE:
<223> OTHER INFORMATION: SYNTHETIC SEQUENCE

<400> SEQUENCE: 57
tacgactcac tagggatc caaaaagaaa aagcagattc aaaaatttag aattcccttt      60
agtgagggtt                                                           70

<210> SEQ ID NO 58
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 58
tacgactcac tagggatc caaagcgaaa aaaaaaaag gcggtaattg aattcccttt       60
agtgagggtt                                                           70

<210> SEQ ID NO 59
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 59
tacgactcac tagggatc caaagaaaaa aagataaac tatggaagag aattcccttt       60
agtgagggtt                                                           70

<210> SEQ ID NO 60
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 60
tacgactcac tagggatc caccatgaaa agcaaaagtt agtcaggttg aattcccttt      60
agtgagggtt                                                           70

<210> SEQ ID NO 61
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 61
tacgactcac tagggatc caagcttcaa aacaaagaca actaggtgag aattcccttt      60
agtgagggtt                                                           70

<210> SEQ ID NO 62
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 62
tacgactcac tagggatc caagcttcaa aacaaagaca actaggtgag aattcccttt      60
agtgagggtt                                                           70
```

<210> SEQ ID NO 63
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 63
tacgactcac tagggatc cagactagac caccaagagc ctacccacag aattcccttt    60
agtgagggtt                                                         70

<210> SEQ ID NO 64
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 64
tacgactcac tagggatc cggtggggta aggtccgagg ggcgtgttgg aattcccttt    60
agtgagggtt                                                         70

<210> SEQ ID NO 65
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 65
tacgactcac tagggatc caatggggca ttggttgaga tgttcgggag aattcccttt    60
agtgagggtt                                                         70

<210> SEQ ID NO 66
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 66
tacgactcac tagggatc cggtgggctg gtcggggtaa ttgatcggag aattcccttt    60
agtgagggtt                                                         70

<210> SEQ ID NO 67
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 67
tacgactcac tagggatc cggtgggggg ggggtgggtt ttggcttggg aattcccttt    60
agtgagggtt                                                         70

<210> SEQ ID NO 68
<211> LENGTH: 70
<212> TYPE: DNA
<213> ORGANISM: Artificial Sequence
<220> FEATURE:
<223> OTHER INFORMATION: SYNTHETIC SEQUENCE

```
<400> SEQUENCE: 68
tacgactcac tatagggatc cggtcttgcg gtaggggtg gcggcgggtg aattcccttt    60
agtgagggtt                                                         70

<210> SEQ ID NO 69
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 69
tacgactcac tatagggatc cgagtgagtt gcttgattcg cccgtaagtg aattcccttt    60
agtgagggtt                                                         70

<210> SEQ ID NO 70
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 70
tacgactcac tatagggatc cttgtttgtt tcacctggtg cgcatatttg aattcccttt    60
agtgagggtt                                                         70

<210> SEQ ID NO 71
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 71
tacgactcac tatagggatc catgtgcgtt tgtgtcgtgg ggggagggtg aattcccttt    60
agtgagggtt                                                         70

<210> SEQ ID NO 72
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 72
tacgactcac tatagggatc caagagaggg ggaggccaga gcaggggag aattcccttt    60 agtgagggtt                                                         70

<210> SEQ ID NO 73
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 73
tacgactcac tatagggatc caagaaagaa gaaggaaaag ggagagggtg aattcccttt    60
agtgagggtt                                                         70

<210> SEQ ID NO 74
<211> LENGTH: 70
```

<212> TYPE: DNA
<213> ORGANISM: Artificial Sequence
<220> FEATURE:
<223> OTHER INFORMATION: SYNTHETIC SEQUENCE

<400> SEQUENCE: 74
tacgactcac tatagggatc cagtaactcc gggagacaat tgggaggatg aattcccttt    60
agtgagggtt    70

<210> SEQ ID NO 75
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 75
tacgactcac tatagggatc caaaagaaca ataagagaga tgaagagtgg aattcccttt    60
agtgagggtt    70

<210> SEQ ID NO 76
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 76
tacgactcac tatagggatc cgcaaataca aaaacgtatg cagagataag aattcccttt    60
agtgagggtt    70

<210> SEQ ID NO 77
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 77
tacgactcac tatagggatc catggcgtag aaggccgatg gagtgagggg aattcccttt    60
agtgagggtt    70

<210> SEQ ID NO 78
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 78
tacgactcac tatagggatc caagaaattt actggcataa gaatctgacg aattcccttt    60
agtgagggtt    70

<210> SEQ ID NO 79
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 79
tacgactcac tatagggatc cgggagacag gaggggaaa gtatgtgtgg aattcccttt    60

-continued agtgagggtt     70

<210> SEQ ID NO 80
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 80
tacgactcac tagggatcc cggcagact aaggccgtac atggggatcg aattcccttt     60
agtgagggtt     70

<210> SEQ ID NO 81
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 81
tacgactcac tagggatcc ccccgccccc acgcctctcc cgcgttttgg aattcccttt     60
agtgagggtt     70

<210> SEQ ID NO 82
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 82
tacgactcac tagggatcc ccccgccccc acgcctctcc cgcgttttgg aattcccttt     60
agtgagggtt     70

<210> SEQ ID NO 83
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 83
tacgactcac tagggatcc cccccccgc cgcggtagat atcacattgg aattcccttt     60
agtgagggtt     70

<210> SEQ ID NO 84
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 84
tacgactcac tagggatcc ctatgtttaa tatatgcggc acggtgtggg aattcccttt     60
agtgagggtt     70

<210> SEQ ID NO 85
<211> LENGTH: 70
<212> TYPE: DNA
<213> ORGANISM: Artificial Sequence
<220> FEATURE:
<223> OTHER INFORMATION: SYNTHETIC SEQUENCE

```
<400> SEQUENCE: 85
tacgactcac tagggatc ccattatgag gcgtgatggc ggggctaagg aattcccttt         60
agtgagggtt                                                              70

<210> SEQ ID NO 86
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 86
tacgactcac tagggatc cttcgttctt ccgtgaatac gaagatgcgg aattcccttt         60
agtgagggtt                                                              70

<210> SEQ ID NO 87
<211> LENGTH: 70
<212> TYPE: DNA
<213> ORGANISM: Artificial Sequence
<220> FEATURE:
<223> OTHER INFORMATION: SYNTHETIC SEQUENCE

<400> SEQUENCE: 87
tacgactcac tagggatc ctccgatcag taagccaaga gaaataaagg aattcccttt         60
agtgagggtt                                                              70

<210> SEQ ID NO 88
<211> LENGTH: 70
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 88
tacgactcac tagggatc caagaangaa aaaggagana ggggggggg aattcccttt          60 agtgagggtt                                                              70
```